US010993996B2

(12) United States Patent
Eren et al.

(10) Patent No.: US 10,993,996 B2
(45) Date of Patent: May 4, 2021

(54) DIGESTIVE ENZYME COMPOSITION SUITABLE FOR ENTERAL ADMINISTRATION

(71) Applicant: Allergan Pharmaceuticals International Limited, Dublin (IE)

(72) Inventors: Devrim Eren, Downingtown, PA (US); Ruth Thieroff-Ekerdt, Mendham, NJ (US); Luigi Boltri, Argrate Brianza (IT); Vincenza Pironti, Milan (IT); Letizia Ubliglia, Vimercate (IT)

(73) Assignee: Allergan Pharmaceuticals International Limited, Dublin (IE)

( * ) Notice: Subject to any disclaimer, the term of this patent is extended or adjusted under 35 U.S.C. 154(b) by 0 days.

(21) Appl. No.: 14/908,642

(22) PCT Filed: Aug. 4, 2014

(86) PCT No.: PCT/US2014/049569
§ 371 (c)(1),
(2) Date: Jan. 29, 2016

(87) PCT Pub. No.: WO2015/020943
PCT Pub. Date: Feb. 12, 2015

(65) Prior Publication Data
US 2016/0166659 A1    Jun. 16, 2016

Related U.S. Application Data

(60) Provisional application No. 61/864,314, filed on Aug. 9, 2013.

(51) Int. Cl.
| *A61K 38/54* | (2006.01) |
| *A61K 38/46* | (2006.01) |
| *A61K 9/00* | (2006.01) |
| *A23L 33/195* | (2016.01) |
| *A23L 33/17* | (2016.01) |
| *A23L 33/00* | (2016.01) |
| *A23L 27/60* | (2016.01) |
| *A61K 9/16* | (2006.01) |
| *A61K 9/50* | (2006.01) |

(52) U.S. Cl.
CPC ............. *A61K 38/54* (2013.01); *A23L 27/60* (2016.08); *A23L 33/17* (2016.08); *A23L 33/195* (2016.08); *A23L 33/40* (2016.08); *A61K 9/0029* (2013.01); *A61K 9/0053* (2013.01); *A61K 9/167* (2013.01); *A61K 9/1682* (2013.01); *A61K 38/465* (2013.01); *C12Y 301/01003* (2013.01); *A23V 2002/00* (2013.01); *A61K 9/5026* (2013.01); *C12Y 302/01* (2013.01); *C12Y 304/21001* (2013.01)

(58) Field of Classification Search
CPC .... A61K 38/465; A61K 38/54; A61K 9/0029; A61K 9/0053; A61K 9/167; A61K 9/1682; A61K 9/5026; A61K 9/5047; C12Y 301/01003; C12Y 302/01; C12Y 304/21001; A23L 1/296; A23L 1/305; A23L 33/17; A23L 33/195; A23L 27/60; A23L 33/40; A23V 2002/00; A61P 1/14
See application file for complete search history.

(56) References Cited

U.S. PATENT DOCUMENTS

| 2,751,330 A | 9/1956 | Reichert |
| 3,844,891 A | 10/1974 | Hess et al. |
| 4,079,125 A | 3/1978 | Sipos |
| 4,237,229 A | 12/1980 | Hartdegen et al. |
| 4,280,971 A | 7/1981 | Wischniewski et al. |
| 4,447,412 A | 5/1984 | Bilton |
| 4,623,624 A | 11/1986 | Schultze |
| 4,704,295 A | 11/1987 | Porter et al. |
| 4,786,505 A | 11/1988 | Lovgren et al. |
| 4,849,227 A | 7/1989 | Cho |
| 4,859,471 A | 8/1989 | Fulberth et al. |
| 5,075,231 A | 12/1991 | Moreau et al. |
| 5,225,202 A | 7/1993 | Hodges et al. |
| 5,260,074 A | 11/1993 | Sipos |

(Continued)

FOREIGN PATENT DOCUMENTS

| AU | 2011309763 B2 | 8/2015 |
| CA | 2263703 A1 | 8/1999 |

(Continued)

OTHER PUBLICATIONS

Shlieout et al. ( Clin. drug investig 2011;31(7);e1-e7.*
A. Aloulou, et al., "In Vitro Comparative Study of Three Pancreatic Enzyme Preparations: Dissolution Profiles, Active Enzyme Release and Acid Stability", Alimentary Pharmacology & Therapeutics, vol. 27, No. 3; Oct. 29, 2007; pp. 283-292.
A. C. Mehta, "Review of analytical methods used in the dissolution testing of pharmaceuticals", Analytical Proceedings Including Analytical Communications, vol. 31, No. 8, Jan. 1, 1994; pp. 245-248.
Alexey Khrenov: "USP Pancrelipase update", Jul. 1, 2009 and Alexey Khrenov: "USP Enzyme WOrkshop: Pancrelipase Update", Jul. 1, 2009.

(Continued)

*Primary Examiner* — Snigdha Maewall
(74) *Attorney, Agent, or Firm* — Nielsen IP Law LLC

(57) ABSTRACT

The present invention is directed to a digestive enzyme composition comprising an enterically coated digestive enzyme product, administrable nutritional medium, and a pharmaceutically acceptable low viscosity oily ingredient. The process for the preparation of the digestive enzyme composition comprises adding an enterically coated digestive enzyme product to a administrable nutritional medium and pharmaceutically acceptable low viscosity oily ingredient. The invention further provides a method for treating a patient suffering from exocrine pancreatic insufficiency related condition comprising administering to the patient a therapeutically effective dose of the digestive enzyme composition by means of a feeding tube.

18 Claims, No Drawings

(56) References Cited

U.S. PATENT DOCUMENTS

| | | | |
|---|---|---|---|
| 5,306,506 A | 4/1994 | Zema et al. | |
| 5,308,832 A | 5/1994 | Garleb et al. | |
| 5,324,514 A | 6/1994 | Sipos | |
| 5,378,462 A | 1/1995 | Boedecker et al. | |
| 5,460,812 A | 10/1995 | Sipos | |
| 5,570,104 A | 10/1996 | Hayashi | |
| 5,578,304 A | 11/1996 | Sipos | |
| 5,665,428 A | 9/1997 | Cha et al. | |
| 5,733,575 A | 3/1998 | Mehra et al. | |
| 5,733,763 A | 3/1998 | Markussen et al. | |
| 5,750,104 A | 5/1998 | Sipos | |
| 5,861,177 A | 1/1999 | Atzl et al. | |
| 5,861,291 A | 1/1999 | Abboudi et al. | |
| 6,051,220 A | 4/2000 | Scharpe | |
| 6,313,102 B1 | 11/2001 | Colaco et al. | |
| 6,318,650 B1 | 11/2001 | Breitenbach et al. | |
| 6,352,974 B1 | 3/2002 | Ghirri et al. | |
| 6,426,091 B1 | 7/2002 | Okumura et al. | |
| 6,607,747 B2 | 8/2003 | Ullah et al. | |
| 6,855,336 B2 | 2/2005 | Chen et al. | |
| 6,955,903 B2 | 10/2005 | Kulkarni et al. | |
| 7,201,923 B1 | 4/2007 | van Lengerich | |
| 7,658,918 B1 | 2/2010 | Ortenzi et al. | |
| 8,071,089 B2 | 12/2011 | Schuler et al. | |
| 8,221,747 B2 | 7/2012 | Ortenzi et al. | |
| 8,246,950 B2 | 8/2012 | Ortenzi et al. | |
| 8,293,229 B2 | 10/2012 | Ortenzi et al. | |
| 8,562,978 B2 | 10/2013 | Ortenzi et al. | |
| 8,562,979 B2 | 10/2013 | Ortenzi et al. | |
| 8,562,980 B2 | 10/2013 | Ortenzi et al. | |
| 8,562,981 B2 | 10/2013 | Ortenzi et al. | |
| 8,784,884 B2 | 7/2014 | Perrett et al. | |
| 2001/0024660 A1 | 9/2001 | Ullah et al. | |
| 2001/0046493 A1 | 11/2001 | Margolin et al. | |
| 2002/0044968 A1 | 4/2002 | van Lengerich | |
| 2002/0054907 A1 | 5/2002 | Devane et al. | |
| 2002/0187536 A1 | 12/2002 | Kulkarni et al. | |
| 2003/0099722 A1* | 5/2003 | Baxter | A23L 33/40 424/679 |
| 2004/0057944 A1 | 3/2004 | Galle et al. | |
| 2004/0101562 A1 | 5/2004 | Maio | |
| 2004/0121010 A1 | 6/2004 | Hirsh et al. | |
| 2004/0197321 A1 | 10/2004 | Sipos et al. | |
| 2004/0213847 A1 | 10/2004 | Matharu et al. | |
| 2005/0019417 A1 | 1/2005 | Ko et al. | |
| 2005/0158299 A1 | 7/2005 | Margolin et al. | |
| 2005/0208133 A1 | 9/2005 | Tsutsumi et al. | |
| 2005/0281876 A1 | 12/2005 | Li et al. | |
| 2006/0121017 A1 | 6/2006 | Margolin et al. | |
| 2006/0198838 A1 | 9/2006 | Fallon | |
| 2007/0025977 A1 | 2/2007 | Mulberg | |
| 2007/0141151 A1 | 6/2007 | Silver et al. | |
| 2007/0148151 A1 | 6/2007 | Frink et al. | |
| 2007/0148152 A1 | 6/2007 | Shlieout et al. | |
| 2007/0190142 A1 | 8/2007 | Breitenbach et al. | |
| 2008/0187525 A1 | 8/2008 | Porubcan | |
| 2008/0199448 A1 | 8/2008 | Ross et al. | |
| 2008/0274174 A1 | 11/2008 | Ortenzi et al. | |
| 2008/0279839 A1 | 11/2008 | Schuler et al. | |
| 2008/0279953 A1 | 11/2008 | Ortenzi et al. | |
| 2008/0299185 A1 | 12/2008 | Ortenzi et al. | |
| 2009/0081184 A1 | 3/2009 | Margolin et al. | |
| 2009/0117180 A1 | 5/2009 | Ortenzi et al. | |
| 2009/0148545 A1 | 6/2009 | Falk et al. | |
| 2009/0226414 A1 | 9/2009 | Tijssen et al. | |
| 2009/0232789 A1 | 9/2009 | Fallon | |
| 2010/0021537 A1 | 1/2010 | Ortenzi et al. | |
| 2010/0239559 A1 | 9/2010 | Freedman et al. | |
| 2010/0270183 A1 | 10/2010 | Ortenzi et al. | |
| 2011/0064799 A1 | 3/2011 | Perrett et al. | |
| 2011/0123605 A1 | 5/2011 | Ortenzi et al. | |
| 2011/0123633 A1 | 5/2011 | Ortenzi et al. | |
| 2011/0123634 A1 | 5/2011 | Ortenzi et al. | |
| 2012/0177629 A1* | 7/2012 | Broussard | A23L 33/40 424/94.21 |
| 2012/0201875 A1 | 8/2012 | Ortenzi et al. | |
| 2013/0251926 A1 | 9/2013 | Wood et al. | |
| 2014/0170212 A1 | 6/2014 | Ortenzi et al. | |
| 2014/0287035 A1 | 9/2014 | Perrett et al. | |
| 2014/0295474 A1 | 10/2014 | Latino et al. | |

FOREIGN PATENT DOCUMENTS

| | | |
|---|---|---|
| CA | 2419572 A1 | 8/2004 |
| CN | 87103560 A | 5/1988 |
| CN | 1235824 A | 11/1999 |
| CN | 1376519 A | 10/2002 |
| CN | 1489476 A | 4/2004 |
| CN | 101249081 A | 8/2008 |
| CN | 101430279 A | 5/2009 |
| CN | 103060296 A | 4/2013 |
| DE | 2730481 A1 | 1/1978 |
| DE | 19907764 A1 | 11/1999 |
| EA | 201290985 A1 | 5/2013 |
| EP | 8780 A2 | 3/1980 |
| EP | 0035780 A1 | 9/1981 |
| EP | 0115023 A2 | 8/1984 |
| EP | 0256127 A1 | 2/1988 |
| EP | 0283442 A1 | 9/1988 |
| EP | 304332 A2 | 2/1989 |
| EP | 0576938 A1 | 1/1994 |
| EP | 0879772 A2 | 11/1998 |
| EP | 1010423 A2 | 6/2000 |
| EP | 1279402 A1 | 1/2003 |
| EP | 1335706 B1 | 4/2005 |
| EP | 1579771 A1 | 9/2005 |
| EP | 1931316 A2 | 6/2008 |
| EP | 1967211 A1 | 9/2008 |
| EP | 2079445 A2 | 7/2009 |
| EP | 2477645 A4 | 7/2012 |
| EP | 2621476 A1 | 8/2013 |
| EP | 2621476 B1 | 7/2014 |
| EP | 2754437 A2 | 7/2014 |
| EP | 2818160 A1 | 12/2014 |
| EP | 2741766 B1 | 10/2015 |
| EP | 2987499 A1 | 2/2016 |
| EP | 3030257 | 6/2016 |
| ES | 489967 A1 | 10/1980 |
| FR | 2313916 A1 | 1/1977 |
| GB | 732951 A | 6/1955 |
| GB | 1509866 A | 5/1978 |
| GB | 2234973 A | 2/1991 |
| JP | S5186113 | 7/1976 |
| JP | S52-3819 A | 1/1977 |
| JP | 58-085159 | 5/1983 |
| JP | S6379589 | 5/1988 |
| JP | H0398580 A | 4/1991 |
| JP | H05-38731 A | 2/1993 |
| JP | 538731 | 10/1993 |
| JP | H05-76928 B2 | 10/1993 |
| JP | H1077236 A | 3/1998 |
| JP | 10-295374 A | 11/1998 |
| JP | H11-514088 A | 11/1999 |
| JP | H11315043 A | 11/1999 |
| JP | 2002506527 A | 2/2002 |
| JP | 2004-513645 A | 5/2004 |
| JP | 2004524838 A | 8/2004 |
| JP | 2006198838 A | 8/2006 |
| JP | 2008516965 A | 5/2008 |
| JP | 4187085 B2 | 11/2008 |
| JP | 2010519217 A | 6/2010 |
| JP | 2011-093845 A | 5/2011 |
| JP | 2013522284 A | 6/2013 |
| JP | 2013530811 A | 8/2013 |
| JP | 2013534141 A | 9/2013 |
| JP | 2013538846 A | 10/2013 |
| JP | 6043929 B2 | 12/2016 |
| KR | 100395722 B1 | 11/2003 |
| KR | 20060127857 A | 12/2006 |
| KR | 100804096 B1 | 2/2008 |
| RU | 94017352 A | 7/1996 |
| RU | 2445952 C2 | 3/2012 |
| TW | 201210517 A | 3/2012 |
| WO | 8705505 A1 | 9/1987 |

(56) References Cited

FOREIGN PATENT DOCUMENTS

| | | |
|---|---|---|
| WO | 90/09428 A1 | 8/1990 |
| WO | 9009440 A1 | 8/1990 |
| WO | 90/15856 A1 | 12/1990 |
| WO | 93/07859 A1 | 4/1993 |
| WO | 93/18753 A1 | 9/1993 |
| WO | 9325669 A1 | 12/1993 |
| WO | 9600773 A1 | 1/1996 |
| WO | 9610995 A1 | 4/1996 |
| WO | 9746658 A1 | 12/1997 |
| WO | 98/01544 A1 | 1/1998 |
| WO | 97/46860 A3 | 2/1998 |
| WO | 98/58254 A1 | 12/1998 |
| WO | 01/25412 A1 | 4/2001 |
| WO | 01/70047 A1 | 9/2001 |
| WO | 0174980 A2 | 10/2001 |
| WO | 0240045 A2 | 5/2002 |
| WO | 02058735 A1 | 8/2002 |
| WO | 2004074470 A1 | 9/2004 |
| WO | 2005042012 A1 | 5/2005 |
| WO | 2005092370 A1 | 10/2005 |
| WO | 2006044529 A1 | 4/2006 |
| WO | 2007013752 A1 | 2/2007 |
| WO | 2007020259 A2 | 2/2007 |
| WO | 2007020260 A2 | 2/2007 |
| WO | 08/017659 A1 | 2/2008 |
| WO | 2008017659 A1 | 2/2008 |
| WO | 2008102264 A2 | 8/2008 |
| WO | 2009083607 A1 | 7/2009 |
| WO | 2009109856 A2 | 9/2009 |
| WO | 2010025126 A1 | 3/2010 |
| WO | 2011035079 A1 | 3/2011 |
| WO | 2011072069 A2 | 6/2011 |
| WO | 2011114224 A1 | 9/2011 |
| WO | 2012019186 A1 | 2/2012 |
| WO | WO-2012019186 A1 * 2/2012 ............. A23L 29/06 | |
| WO | 2012042372 A1 | 4/2012 |
| WO | 2012052853 A2 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |

OTHER PUBLICATIONS

"Dissolution Toolkit—Procedures for Mechanical Calibration and Performance Verification Test", USP (U.S> Pharmacopeia), Mar. 22, 2010.
New Zealand First Examination Report corresponding to New Zealand Application No. 620329, dated Oct. 16, 2014; 2 pages.
Colombian Office Action with English translation, dated Oct. 29, 2014, corresponding to Colombian Application No. 14-33910; 17 total pages including English translation.
Coutlee, et al., "Comparison of Colorimetric, Fluorescent, and Enzymatic Amplification Substrate Systems in an Enzyme Immunoassay for Detection of DNA-RNA Hybrids", Journal of Clinical Microbiology, vol. 27, No. 5, May 1989, pp. 1002-1007.
Fuhrmann, et al., "In Vivo Fluorescence Imaging of Exogenous Enzyme Activity in the Gastrointestinal Tract", Proceedings of the National Academy of Sciences of the USA, vol. 108, No. 22, May 2011; pp. 9032-9037.
Zhang, et al., "Quantitative Fluorescence Correlation Spectroscopy Reveals a 1000-Fold Increase in Lifetime of Protein Functionality", Biophysical Journal, vol. 95, Oct. 2008; pp. 3439-3446.
(Guidance for Industry) "SUPAC-MR: Modified Release Solid Oral Dosage Forms Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997.
Australian Patent Examination Report No. 1, dated May 20, 2014, corresponding to Australian Application No. 2012293325; 3 pages.

Chinese Office Action dated Dec. 2, 2014 (with No English translation), corresponding to Chinese Application No. 201280040203.2; 6 pages.
Colombian Office Action (English Summary), corresponding to Colombian Application No. 13-66300; 2 pages.
Eurasian Office Action dated Jun. 30, 2014 (with English translation), corresponding to Eurasian Application No. 201390409; 5 total pages.
Handbook of Pharmaceutical Excipients, Fifth Edition, Edited by Raymond C. Rowe, et al. 4 pages.Rowe, et al., Handbook of Pharmaceutical Excipients, 4 pages.
Austrailian Patent Examination Report No. 1, dated Oct. 14, 2014, corresponding to Austrailian Application No. 2011309763; 3 pages.
European Search Report corresponding to European Application No. 14176579.2, dated Nov. 28, 2014, 4 pages.
English translation of Colombian Office Action, corresponding to Colombian Application No. 13-066300; 7 pages.
Chinese Office Action (No English translation), dated Jan. 6, 2015, corresponding to Chinese Application No. 201180055719.X; 18 pages.
Masaki Hasegawa, Direct Compression Microcrystalline Cellulose Grade 12 versus Classic Grade 102, Pharmaceutical Technology, pp. 50-60, May 2002.
Australian Patent Examination Report No. 1 corresponding to Australian Application No. 2010295494, dated Apr. 28, 2014; 3 pages.
Extended European Search Report, corresponding to European Application No. 10817867.4, dated May 26, 2014; 6 pages.
Symersky T., et al. "An Explorative Study on the Effect of Enzyme Supplementation in Patients Recovered From Acute Pancreatitis", Gastroenterology 2004; 126 (4 suppl 2): A85, Abstract 653.
Taiwanese Office Action dated Jul. 21, 2014; 6 pages.
Tawianese Search Report corresponding to Taiwanese Application No. 099131496, dated Jul. 16, 2014, 1 page.
Russian Office Action (with English Translation) corresponding to Russian Application No. 2012113253, dated Jul. 7, 2014; 8 total pages.
Colombian Office Action issued by the Colombian Patent Office dated Aug. 22, 2014 (with no English translation), corresponding to Colombian Application No. 12-50658, 9 pages.
Chilean Office Action (without English Translation) dated Oct. 8, 2014, corresponding to Chilean Patent Application No. 00658-2012; 8 pages.
Japanese Notice of Rejection dated Sep. 24, 2014 (with English Translation), corresponding to Japanese Application No. 2012-529909; 6 pages.
Chinese Office Action (with No English translation), corresponding to Chinese Application No. 201080041366.3, dated Nov. 24, 2014; 3 pages.
Russian Office Action (with English translation), corresponding to Russian Application No. 2012113253, dated Nov. 25, 2014; 11 total pages.
Taiwanese Office Action (with English translation), corresponding to Taiwanese Application No. 099131496, dated Nov. 26, 2014; 10 total pages.
Pakastan Examination Report, corresponding to Pakistan Application No. 804/2010; 1 page.
English translation of Israeli Office Action, corresponding to Israeli Application No. 218656, dated Nov. 23, 2014; 2 pages.
Eurasian Office Action (with English Translation) dated Jan. 30, 2015, corresponding to Eurasian Application No. 201390409/28; 4 total pages.
Avicel-FMC, Avicel product sheet, Apr. 22, 2010.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-2009-7019590; 6 total pages.
Non-patent literature cited during the Appeal Procedure (universitatbonn) (D22), dated Jun. 17, 2010; 6 pages.
Letter dated Aug. 5, 2010, relating to the Appeal Procedure (Eisenfuhr Speiser); 10 pages.

(56) References Cited

OTHER PUBLICATIONS

Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Kahn, et al., Bovine Pancreatic Lipase1. II. Stability and Effect of Activators and Inhibitors, Journal of Dairy Science, vol. 59, No. 5, pp. 840-846.
Worthington Biochemical Corporation, Lipase—Worthington Enzyme Manual, Triacylglycerol acylhydrolase, (D14); www.worthington-biochem.com; Jun. 24, 2009; 2 pages.
Caelo, Macrogol 4000 Pulver, Sicherheitsdatenblatt, Seite1, von 3, (D15) dated Aug. 4, 2008; 3 pages.
Answers.com, Stir: Difinition, Synonyms of the word "Stir" from Answers.com, (D16), Jun. 24, 2009; 9 pages.
Office Action issued by the U.S. Patent and Trademark Office dated Apr. 1, 2009, corresponding to U.S. Appl. No. 10/416,702, 24 pages.
Final Office Action issued by the U.S. Patent and Trademark Office dated Jul. 14, 2008, corresponding to U.S. Appl. No. 10/416,702, 12 pages.
Fuhrmann, Vorlesungen uber, Technische Mykologie, Verlag Gustav Fisher 1913, 80; (D19); 4 pages.
Mesh to Micron Conversion Chart—Fluideng.com, Copyright 2002—Property of TM Industrial Supply, Inc.; (D20); http://www.fluideng.com/FE/meshmicron.html; 1 page.
English Translation of Example 3 of Priority Document Italian Patent Application No. MI2000 A 0022456; (D21); 1 page.
Summary of facts and submissions, Grounds for the Decision (Annex)—opposition, corresponding to Application No. 01 994 654.0, dated Feb. 23, 2009; 9 pages.
Interlocutory Decision in Opposition proceedings, corresponding to Application No. 01 994 654.0-2107, dated Feb. 23, 2009; 2 pages.
Druckexemplar, relating to EP1 335 706 B1, 8 pages.
Provision of the minutes in accordance with Rule 124(4) EPC, dated Feb. 23, 2009, corresponding to Application No. 01 994 654.0-2107; 12 pages.
Non-patent literature, dated Jul. 30, 2012, relating to the Appeal Procedure, (Eisenfuhr Speiser); 7 pages.
Letter from Botti & Ferrari, dated Jun. 27, 2012, relating to the Appeal Procedure, 10 pages.
Non-patent literature cited during the Appeal Procedure, (Eisenfuhr Speiser), Grounds of Appeal, dated Jun. 30, 2009; 24 pages.
Letter from Botti & Ferrari, dated Sep. 18, 2009, relating to the Appeal Procedure, 15 pages.
Main Request, Claims with revisions, relating to Appeal Procedure; 1 page.
Description, relating to EP 1 335 706, relating to the Appeal Procedure; 1 page.
Main Request, Claims 1-7, relating to Appeal Procedure; 2 pages.
Royce, et al., Alternative Granulation Technique: Melt Granulation, Drug Development and Industrial Pharmacy, (D4) 22(9&10), 917-924; Copyright 1996 by Marcel Dakker, Inc.
Lombroso, "About the Destruction of the Pancreatic Enzymes by Means of Heat and the Substances that Hamper Such Action", Archivio di Farmacologia Sperimentale e Scienze Affini, Laboratory of Physiology of the R. University of Rome; 14 pages.
Novozymes—Savinase, novozymes, Rethink Tomorrow, Annex 1, A Hard-working, robust protease used to remove protein-based stains; 1 page.
Notice of Opposition to a European Patent and opposition documents related to Patent No. EP 1 335 706 B1, (Opposition file history as of Jan. 14, 2009, excluding non-duplicative, non-administrative documents; (92 total pages).
Non-patent literature dated Sep. 30, 2011, relating to the Appeal Procedure, (Eisenfuhr Speiser); 2 pages.
Non-patent literature cited during the Appeal Procedure, (universitatbonn) (D23), dated Sep. 20, 2011; 15 pages.
Non-patent literature cited during the Appeal Procedure, (One Step Ahead, Granulation and drying for all types of products), Rotolab, (D24); 8 pages.
Sincero, et al., "Detection of hepatitis A virus (HAV) in oysters (*Crassostrea gigas*)" Water Research, Elsevier, Amsterdam, NL, vol. 40, No. 5, Mar. 1, 2006; pp. 896-902.
Langeveld, et al, "Inactivated recombinant plant virus protects dogs from a lethal challenge with canine parvovirus" Vaccine, Butterworth Scientific Guildford, GB, vol. 19, No. 27, Jun. 14, 2001, pp. 3661-3670.
Singh, et al., "Canine parvovirus-like particles, novel nanomaterial for tumor targeting" Journal of Nanobiotechnology 2006, vol. 4, No. 2, dated Feb. 13, 2006; 11 pages.
Shieh, et al., "A method to detect low levels of enteric virus in contaminated oysters", Applied and environmental Microbiology, vol. 65, No. 11, Nov. 1999, pp. 4709-4714.
Bergeron, et al., Genomic Organization and Mapping of Transcription and Translation Products of the NADL-2 Strain of Porcine Parvovirus, Virology, 1993, 197(1): pp. 86-98.
Bergeron, J., Hebert, B. and Tijssen, P. (1996), Genomic Organization of the Kresse Strain of Porcine Parvovirus: Identification of the Allotropic Determinant and Comprison with Those of NADL-2 and Field Isolates, Journal of Virology 70, pp. 2508-2515.
Simpson, et al., "The Structure of Porcine Parvovirus: Comparison With Related Viruses", J. Mol. Biol., 2002, 315(5); pp. 1189-1198.
Szelei, et al., "Porcine Parvovirus". In: Kerr, et al., eds, Parvoviruses, London: Hodder Arnold; 2006; pp. 434-445.
Canaan, et al., 2004, "Interfacial Enzymology of Parvovirus Phospholipases A2", Journal of Biologizal Chemistry 279(15), pp. 14502-14508.
Zadori, et al., 2001, "A Viral Phospholipase A2 is Required for Parvovirus Infectivity", Developmental Cell 1: pp. 291-302.
Zadori, et al., 2005, "SAT: a Late NS Protein of Porcine Parvovirus", Journal of Virology 79(20); pp. 13129-13138.
Mullendore, et al., Improved Method for the Recovery of Hepatitis A virus from oysters, Journal of Virological Methods 94, pp. 25-35 (2001).
Sair, et al., "Improved Detection of Human Enteric Viruses in Foods by RT-PCR", Journal of Virological Methods 100, pp. 57-69 (2002).
Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).
International Written Opinion of the International Searching Authority and International Search Report dated Jan. 19, 2010, corresponding to International Application No. PCT/IB2009/000472; 7 total pages.
US Pharmacopeia, Chapter 786, Particle Size Distribution Estimation by Analytical Sieving, Web download, Jun. 26, 2009; 5 pages.
Gohel, "A Review of Co-Processed Directly Compressible Excipients," J. Pharm. Pharmaceutical Sciences, 8(1); pp. 76-93; (2005).
Priority Document, Italian Patent No. MI2000 A 002456, 25 pages.
International Search Report, dated Jun. 23, 2014, corresponding to International Application No. PCT/IB2014/059722; 4 pages.
Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.
Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.
International Search Report and Written Opinion of the International Searching Authority, corresponding to International Application No. PCT/US14/63984, dated Mar. 13, 2015; 10 total pages.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.
International Search Report and Written Opinion of the International Searching Authority, dated Mar. 2, 2015, corresponding to International Application No. PCT/IB2014/002583; 13 total pages.

(56) References Cited

OTHER PUBLICATIONS

Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.
International Search Report, and Written Opinion of the International Searching Authority, corresponding to International Application No. PCT/US14/49569, dated Nov. 14, 2014; 8 total pages.
Queensland Government, "Tube Feeding at Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009, 15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
Chinese First Office Action and Search Report (English translations), dated Apr. 3, 2015, corresponding to Chinese Patent Application No. 201410059861.7; 23 total pages.
Israeli Office Action dated May 10, 2015 (No English translation), corresponding to Israeli Patent Application No. 200407; 2 pages.
European extended Search Report, dated Jun. 2, 2015, corresponding to European Patent Application No. 14150794.7; 10 pages.
Japanese Office Action (No English translation), dated May 12, 2015, corresponding to Japanese Patent Application No. 2013-530811; 3 pages.
Canadian Office Action dated Jul. 3, 2015, corresponding to Canadian Patent Application No. 2,774,269; 4 pages.
Japanese Final Office Action (No English translation), dated Jul. 7, 2015, corresponding to Japanese Patent Application No. 2012-529909; 3 pages.
Chilean Office Action (without English Translation) dated Jul. 22, 2015, corresponding to Chilean Patent Application No. 00658-2012; 8 pages.
Communication of a Notice of Oppoistion to a European Patent Application and opposition documents related to Patent Application No. EP 117885223.3, dated Aug. 5, 2015 (678 total pages).
Arbocel Product Sheet.
Wikipedia Search Result for Mehl (No English translation).
U.S. Appl. No. 61/389,037, filed Oct. 1, 2010 (prosecution history).
Chinese Office Action (No English translation available), dated Jul. 28, 2015, corresponding to Chinese Patent Application No. 201180055719.X; 13 pages.
Russian Office Action (with English translation), dated Jun. 15, 2015, corresponding to Russian Patent Appplication No. 2014104591/15; 10 total pages.
European Communication dated Jul. 6, 2015, corresponding to European patent application No. 14150794.7; 2 pages.
Korean Notice of Preliminary Rejection (with English translation), dated Jun. 12, 2015, corresponding to Korean patent application No. 10-2015-7004820; 16 total pages.
Australian Patent Examination Report No. 1, dated Jul. 6, 2015, corresponding to Australian Patent Application No. 2014203364; 4 pages.
Canadian Office Action and Examination Search Report dated Sep. 3, 2015, corresponding to Canadian Patent Application No. 2,677,989; 4 total apges.
Japanese Decision of Rejection (with English translation) dated Sep. 25, 2015, corresponding to Japanese Applcation No. 2013-265143; 9 total pages.
English translation of Chinese Second Office Action dated Dec. 21, 2015, corresponding to Chinese Application No. 201410059861.7; 5 pages.
Taiwanese Office Action (with English translation), dated Nov. 3, 2015, corresponding to Taiwanese Application No. 102138934; 16 total pages.
International Preliminary Report on Patentability and Written Opinion of the International Searching Authoirty, corresponding to International Application No. PCT/IB2014/059722, dated Sep. 15, 2015; 9 Pages.
Australian Patent Examination Report 1, dated Sep. 15, 2015, corresponding to Australian Patent Application No. 2014253526; 3 pages.
Eurasian Search Report (with English translation) issued by the EUrasian Patent Organization (EAPO) dated Sep. 16, 2015, corresponding to Eurasian Patent Application No. 201590836; 4 total pages.
Eurasian Search Report (with English translation) issued by the EUrasian Patent Organization (EAPO) dated Sep. 16, 2015, corresponding to Eurasian Patent Application No. 201590835; 4 total pages.
Ukrainian Office Action (with English Translation) dated Sep. 23, 2015, corresponding to Ukraine Application No. a 2013 03847; 11 total pages.
Colombian Office Action (No English Translation Available), dated Sep. 30, 2015, corresponding to Colombian Application No. 14-33910; 11 pages.
Japanese Office Action (with English translation), dated May 12, 2015, corresponding to Japanese Patent Application No. 2013-530811; 8 total pages.
International Search Report and Written Opinion of the International Searching Authority dated Nov. 20, 2015, corresponding to International Application No. PCT/IB2015/001237; 17 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
Eurasian Office Action (With English Translation) dated Oct. 30, 2015, correpsonding to Eurasian Application No. 201390409/28; 4 total pages.
English translation of Israeli Office Action dated Jan. 11, 2016, corresponding to Israeli Patent Application No. 225504; 3 pages.
Russian Office Action (with English translation), dated Oct. 29, 2015, corresponding to Russian Application No. 2014104591; 7 total pages.
Mesh to Micron Conversion Chart—Fluideng.com, Copyright 2002—Property of TM Industrial Supply, Inc.; (D20); http://www.fluideng.com/FE/meshmicron.html; Jun. 30, 2009; 1 page.
International Preliminary Report on Patentability and Written Opinion of the International Searching Authority, dated Feb. 9, 2016, corresponding to International Application No. PCT/US2014/049569; 7 total pages.
International Preliminary Report on Patentability and Written Opinion of the International Searching Authority, dated Jan. 26, 2016, corresponding to International Application No. PCT/IB2014/002583; 10 total pages.
European Search Report dated Jan. 22, 2016, corresponding to European Application No. 15178147.3; 9 pages.
Communication of the Board of Appeal, corresponding to Appeal No. T2255/12-3.3.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Botti & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patent No. 1 931 316, dated May 2, 2012; 1 page.

(56) References Cited

OTHER PUBLICATIONS

Non-Patent Literature document—"Submission in opposition proceedings," issued by the European Patent Office, corresponding to European Patent No. 1 931 316, dated May 2, 2012; 1 page.
Non-Patent Literature document—"Reply to summons to attend oral proceedings; filing of new main claim request," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.
Non-Patent Literature document—Letter from Europatent to European Patent Office, corresponding to European Patent No. 1 931 316, dated Feb. 6, 2012; 1 page.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1(2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Non-Patent Literature document—"Notice of Opposition against the European Patent EP-B-1 931 316", (letter from Botti & Ferrari to the European Patent Office), dated Nov. 15, 2010, 12 pages.
Colombian Office Action (No English translation available), dated Feb. 19, 2016, corresponding to Colombian Application No. 14-026502; 8 pages.
Non-Patent Literature Document—"Aqueous Coating—Aquacoat ECD," FMC Biopolymer; 12 pages.
Non-Patent Literature document—"Brief Communication," dated Feb. 10, 2011, issued by the European Patent Office, corresponding to European Application No. 06778240.9 (European Patent No. 1 931 316); 1 page.
Non-Patent Literature document—"Vollmacht Authorisation Pouvoir," (German document—Power of Representation before the EPO for European Patent No. 1 931 316, dated Sep. 13, 2011; 3 total pages.
Non-Patent Literature document—"Claims—First Auxiliary Request" and "Claims—Second Auxiliary Request," dated Sep. 2011, corresponding to Opposition Proceedings of European Patent No. 1 931 316; 12 total pages.
Non-Patent Literature document—"Brief Communication—Main Request,", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to Euoprean Patent No. 1 931 316, dated Jan. 21, 2010; 2 pages.
Non-Patent Literature document—"A2PAMPHLET," related to WO 2007/020259 (PCT/EP2006/065311), printed on May 19, 2008; 29 total pages.
Non-Patent Literature document—"Claims (EP 06 778 240)," printed Sep. 25, 2008; 12 total pages.
Naftifine HCI—MSDS—Material Safety Data Sheet, created Jun. 23, 2004; http://pharmacycode.com/msds/Naftifine_HCI; 4 pages.

Australian Patent Examination Report No. 2, dated Feb. 25, 2016, corresponding to Australian Application No. 2014203364; 5 pages.
Egyptian Office Action (No English translation available), dated Mar. 20, 2016, corresponding to Egyptian Application No. PCT 1257/2009; 5 pages.
Japanese Office Action (with English translation), dated Mar. 1, 2016, corresponding to Japanese Application No. 2014-524476; 5 total pages.
Chinese Office Action (No English translation available), dated Feb. 15, 2016, corresponding to Chinese Application No. 201180055719.X; 14 pages.
"Polymer Science in Pharmaceutics", Junmin Zheng, China Medical Science Press, pp. 113-114, Jan. 31, 2009)—Article Unavailable.
Mexican Office Action (No English translation available), corresponding to Mexican Application No. MX/a/2013/003627, dated Mar. 10, 2016; 2 pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Malaysian Office Action dated Mar. 31, 2016, corresponding to Malaysian Application No. PI 2012001215; 3 pages.
Israeli Office Action (No English translation available), dated Apr. 3, 2016, corresponding to Israeli Application No. 218656; 2 pages.
Sankalia M.G. et al., "Papain Entrapment in Alginate Beads for Stability Improvement and Site-Specific Delivery: Physicochemical Characterization and Factorial Optimization Using Neural Network Modeling," AAPS PharmSciTech., 2005; vol. 6, No. 2, Article 31; pp. E209-E222.
Scheich C. et al., "An Automated In Vitro Protein Folding Screen Applied to a Human Dynactin Subunit," Protein Science, 2004, vol. 13; pp. 370-380.
Miller D.A. et al., "Evaluation of the USP Dissolution Test Method a for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; pp. 12488-12496.
Eurasian Office Action (with English translation), dated May 30, 2016, corresponding to Eurasian Application No. 201590835/28; 4 total pages.
Eurasian Office Action (with English translation), dated May 30, 2016, corresponding to Eurasian Application No. 201590836/28; 4 total pages.
Eurasian Office Action (with English translation), dated Jun. 8, 2016, corresponding to Eurasian Application No. 201390409/28; 4 total pages.
Chinese Office Action (No English language translation available), dated Jul. 5, 2016, corresponding to Japanese Application No. 201180055719.X; 14 pages.
Taiwanese Office Action with English tranlsation of Search Report, dated May 13, 2016, corresponding to Taiwaense Application No. 099131496; 5 total pages.
Australian Patent Examination Report No. 3, dated Jun. 28, 2016, corresponding to Australian Application No. 2014203364; 3 pages.
English translation of Chinese Third Office Action, dated Jun. 28, 2016, corresponding to Chinese Application No. 201410059861.7; 4 pages.
Korean Office Action (with English translation) dated May 16, 2016, corresponding to Korean Application No. 10-2015-7004820; 10 total pages.
Australian Patent Examination Report No. 1, dated Sep. 21, 2016, corresponding to Australian Application No. 2015243026; 3 pages.
Chilean Office Action (No English translation available), dated Aug. 22, 2016, corresponding to Chilean Patent Application No. 2014-00315; 8 pages.
English translation of Israeli Office Action dated Aug. 30, 2016, corresponding to Israeli Application No. 243627; 2 pages.

(56) References Cited

OTHER PUBLICATIONS

Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.
Tolin et al., "Purification and Serology of Peanut Mottle Virus", The American Phytopathological Society, vol. 73, No. 6, 1983; pp. 899-903.
Casas et al., "Detection of enterovirus and hepatitis A virus RNA in mussels (*Mytilus* spp.) by reverse transcriptase-polymerase chain reaction", Journal of Applied Microbiology, vol. 90, 2001; pp. 89-95.
Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 8, Aug. 1988; pp. 1983-1988.
Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.
International Search Report, Written Opinion and International Preliminary Report on Patentability based on International Application No. PCT/IB2008/000770, dated Jun. 3, 2009; 13 Pages.
Krishnamurty et al., "Delayed release pancrelipase for treatment of pancreatic exocrine insufficiency associated with chronic pancreatitis," Therapeutics and Clinical Risk Management, (2009:5) pp. 507-520.
Drugs@FDA Glossary of Terms, printed Nov. 20, 2009; http://www.fda.gov/Drugs/InformationonDrugs/ucm079436.htm; 7 pages.
Guidance for Industry #191, Changes to Approved NADAs—New NADAs vs. Category II Supplemental NADAs, Final Guidance, U.S. Department of Health and Human Services, Food and Drug Administration, Center for Veterinary Medicine, Released Nov. 19, 2009: 25 pages.
Singapore Written Opinion, corresponding to Singapore Patent Application No. 200905385-1, issued by the Austrian Patent Office dated Dec. 16, 2010; 6 pages.
Hageman, "The Role of Moisture in Protein Stability," Drug Development and Industrial Pharmacy, vol. 14, No. 14, (1988); pp. 2047-2070.
Maul and Schmidt, "Influence of different-shaped pigments on bisacodyl release from Eudragit L 30 D," International Journal of Pharmacetuics, vol. 118, No. 1, May 1, 1995; pp. 103-112.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, pp. 498-506.
Felton and McGinity, "Influence of Insoluble Excipients on Film Coating Systems," Drug Development and Industrial Pharmacy, vol. 28, No. 3; pp. 225-243.
Parker et al., "Effects of Solids-Loading on Moisture Permeability Coefficients of Free Films," Journal of Pharmaceutical Sciences, vol. 63, No. 1 (Jan. 1974); pp. 119-125.
Thoma and Bechtold, "Influence of aqueous coatings on the stability of enteric coated pellets and tablets," European Journal of Pharmaceutics and Biopharmaceutics, vol. 47, (1999), pp. 39-50.
Nordmark pancreatin brochure, Products all over the World, (publication year unknown); 7 pages.
Australian First Examination Report, dated Mar. 23, 2012, corresponding to Australian Patent Application No. 2008218595; 2 pages.
English Translation of Second Chinese Office Action, dated Apr. 12, 2012, corresponding to Chinese Patent Application No. 200880012762.6; 5 pages.
European Communication, dated Jan. 3, 2012, corresponding to European Patent Application No. 08719392.6; 7 pages.
European Communication, dated Aug. 1, 2012, corresponding to European Patent Application No. 08719392.6; 7 pages.
New Zealand First Examination Report, dated Aug. 26, 2010, corresponding to New Zealand Patent Application No. 579047; 3 pages.
New Zealand Second Examination Report, dated Dec. 15, 2011, corresponding to New Zealand Patent Application No. 579047; 2 pages.
New Zealand First Examination Report, dated Feb. 29, 2012, corresponding to New Zealand Patent Application No. 598477; 1 page.
Singapore Second Written Opinion, dated Nov. 22, 2011, corresponding to Singapore Patent Application No. 200905385-1; 6 pages.
U.S. Office Action, dated Mar. 20, 2012, corresponding to U.S. Appl. No. 12/034,480; 7 pages.
U.S. Office Action, dated Oct. 14, 2011, corresponding to U.S. Appl. No. 12/034,480; 15 pages.Office Action for U.S. Appl. No. 12/034,480, dated Oct. 14, 2011, 15 pages.
U.S. Office Action, dated Mar. 19, 2012, corresponding to U.S. Appl. No. 12/034,488; 8 pages.
U.S. Office Action, dated Oct. 25, 2011, corresponding to U.S. Appl. No. 12/034,488; 14 pages.
U.S. Office Action, dated Jan. 4, 2012, corresponding to U.S. Appl. No. 12/034,491; 7 pages.
U.S. Office Action, dated Jun. 23, 2011, corresponding to U.S. Appl. No. 12/034,491; 7 pages.
U.S. Office Action, dated Jun. 26, 2012, corresponding to U.S. Appl. No. 13/019,844; 15 pages.
U.S. Office Action, dated May 24, 2012, corresponding to U.S. Appl. No. 13/019,856; 9 pages.
U.S. Office Action, dated May 23, 2012, corresponding to U.S. Appl. No. 13/019,860; 5 pages.
U.S. Office Action, dated Jul. 2, 2012, corresponding to U.S. Appl. No. 12/832,596; 11 pages.
International Search Report and Written Opinion, dated Oct. 22, 2012, corresponding to International Application No. PCT/US2010/049203; 6 pages.
Canadian Office Action, dated May 6, 2014, corresponding to Canadian Application No. 2,677,989, 2 pages.
Colombian Office Action (with No English translation), dated May 26, 2014, corresponding to Colombian Application No. 09.101.677, 4 pages.
Costa Rica Preliminary Technical Report—1st Phase, corresponding to Costa Rica Application No. 11031, issued Jun. 12, 2014; 11 total pages.
European Communication dated Apr. 8, 2014, corresponding to European Application No. 08 719 392.6, 6 pages.
Indian Office Action, dated Oct. 17, 2014, corresponding to Indian Application No. 5854/DELNP/2009; 4 pages.
Japanese Decision of Rejection and Decision of Dismissal of Amendment (with English translations), dated Aug. 25, 2014, corresponding to Japanese Application No. 2009-549868; 9 total pages.
Singapore Search Report, dated Apr. 7, 2014 and Singapore Written Opinion, dated Apr. 28, 2014, corresponding to Singapore Application No. 2012091583; 11 total pages.
Japanese Office Action (with English translation), dated Jan. 19, 2015, corresponding to Japanese Application No. 2013-265143, 11 total pages.
Taiwanese Office Action and Search Report (with English translation, dated Oct. 3, 2014, corresponding to Taiwanese Application No. 102138934; 10 total pages.
Colombian Office Action (with No English translation), dated Sep. 23, 2014, corresponding to Colombian Application No. 14.026.502, 4 pages.
The Decision of the Enlarged Board of Appeal, dated Nov. 22, 2013, 18 pages.
The Minutes of the Oral Proceedings of Nov. 22, 2013, 6 pages.
Communication from the Enlarged Board of Appeal pursuant to Articles 13 and 14(2) RPEBA, dated Sep. 17, 2013; 6 pages.
Letter from Botti & Ferrari regarding a Petition for Review of Decision T0977/09-3.3.02, European Patent No. 1 335 706 in the name of Aptalis Pharma S.r.l., dated May 15, 2013; 12 pages.

(56) References Cited

OTHER PUBLICATIONS

Termination of Opposition Proceedings of Patent No. 01994654.0-1456 / 1335706 with Revocation of the Patent, dated Mar. 14, 2013; 2 pages.
Decision dated Nov. 30, 2012; 28 pages.
The Minutes of the Oral Proceedings of Nov. 30, 2012; 18 pages.
International Search Report, International Preliminary Report on Patentability and Written Opinion of the International Searching Authority, corresponding to International Application No. PCT/IB2012/054050, dated Nov. 14, 2012; 11 total pages.
European Extended Search Report dated Feb. 15, 2017, corresponding to European Application No. 14833670.4; 9 pages.
"Ensure Plus HN", ip.com Journal, ip.com Inc., West Henrietta, NY, US, Feb. 9, 2002 (This document completes the disclosure of US2012/177629 with respect to the composition of the product Ensure Plus); 1 page.
Sackman et al., "Does Mixing Pancreatic Enzyme Microspheres (Pancrease) with Food Damage the Enteric Coating?", Journal of Pediatric Gastroenterology and Nutrition, Jan. 1, 1982; pp. 333-335.
Shlieout et al., "Administration of CREON Pancrelipase Pellets via Gastrostomy Tube is Feasible with no Loss of Gastrict Resistance or Lipase Activity—An In Vitro Study", Clinical Drug Investigation, vol. 31, No. 7, Jan. 1, 2011; pp. e1-e7.
English translation of Israeli Office Action, dated Sep. 29, 2016, corresponding to Israeli Application No. 241540; 2 pages.
European Communication dated Jan. 2, 2017, corresponding to European Application No. 14 717 867.7; 5 pages.
European Communication and Supplemental Partial European Search Report, dated Nov. 14, 2016, corresponding to European Application No. 14859866.7, 9 pages.
European Communication dated Sep. 29, 2016, corresponding to European Application No. 10 817 867.4; 3 pages.
Korean Office Action (with English translation), dated Nov. 11, 2016, corresponding to Korean Application No. 10-2012-7009516; 12 total pages.
Israeli Office Action dated Jan. 16, 2017, corresponding to Israeli Application No. 218656; 2 pages.
Israeli Office Action dated Jan. 17, 2017, corresponding to Israeli Application No. 245875; 2 pages.
Mexican Office Action (no English translation available), dated Aug. 19, 2016 (received Sep. 8, 2016), corresponding to Mexican Application No. MX/a/2013/003627; 3 pages.
Eurasian Office Action (with English translation), dated Dec. 19, 2016, corresponding to Eurasian Application No. 201390409/28; 4 total pages.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, (1997); pp. 498-506.
Handbook of Pharmaceutical Excipients, Fifth Edition, Edited by Raymond C. Rowe, et al. (Aug. 2005) 4 pages.
Kahn, et al., Bovine Pancreatic Lipase1. II. Stability and Effect of Activators and Inhibitors, Journal of Dairy Science, vol. 59, No. 5, Apr. 1975; pp. 840-846.
Description, relating to EP 1 335 706, paragraphs [0022] through [0036], relating to the Appeal Procedure (E8); 1 page.
Novozymes—Savinase, novozymes, Rethink Tomorrow, Annex 1, A Hard-working, robust protease used to remove protein-based stains; Copyright 2008 Novozymes; 1 page.
Non-patent literature cited during the Appeal Procedure, (One Step Ahead, Granulation and drying for all types of products), Rotolab, (D24); Jun. 28, 2012; 8 pages.
Arbocel Product Sheet, J. Rettenmaier & Bohne Gmbh & Co. (JRS); 1 page.
Alexey Khrenov, "USP Enzyme Workshop: Pancrelipase update", (Jul. 1, 2009), URL:http://www.usp.org/meetings-courses/workshops/past-usp-workshops/usp-enzyme-workshop, (Nov. 6, 2012), XP055043191 [A] 1-26 the whole document (Document Not Available).

Wikipedia Search Result for Mehl (Flour in English) (English translation also attached); printed from www.wikipedia.com on Feb. 2, 2017; 18 total pages.
European Communication dated Mar. 2, 2017, corresponding to European Application No. 15 178 147.3; 6 pages.
English translation of a UAE Search Report and Examination Report issued by the UAE Patent Office dated Oct. 31, 2016, corresponding to UAE Application No. 743/2009; 15 total pages.
Canadian Office Action and Examination Search Report, dated Nov. 18, 2016, corresponding to Canadian Application No. 2,677,989; 3 total pages.
English translation of Chinese Office Action dated Jan. 20, 2017, corresponding to Chinese Application No. 201410059861.7; 4 total pages.
Australian Examination Report No. 1, dated Feb. 8, 2017, corresponding to Australian Application No. 2016204414; 5 pages.
Nakamura et al., "Effects of High-Lipase Pancreatin on Fecal Fat, Neutral Sterol, Bile Acid, and Short-Chain Fatty Acid Excretion in Patients with Pancreatic Insufficiency Resulting from Chronic Pancreatitis," International Journal of Pancreatology, Feb. 1998; vol. 23, No. 1; pp. 63-70.
G. J. Peschke, "Active Components and Galenic Aspects of Enzyme Preparations," Pancreatic Enzymes in Health and Disease, Springer-Verlag Berlin Heidelberg, 1991; pp. 55-64.
European Communication dated Apr. 11, 2017, corresponding to Eurpeoan Application No. 14859866.7; 1 page.
European Search Report dated Mar. 24, 2017, corresponding to European Application No. 14859866.7; 21 total pages.
Australian Examination Report, dated Apr. 10, 2017, corresponding to Australian Application No. 2016216662; 3 pages.
European Communication dated May 19, 2017, corresponding to European Application No. 10817867.4; 3 pages.
Japanese Office Action (no English translation available), dated Jul. 4, 2017, corresponding to Japanese Application No. 2016-196831.
Canadian Office Action and Examination Search Report, dated Aug. 16, 2017, corresponding to Canadian Application No. 2,812,862; 4 total pages.
Eurasian Office Action (with English Translation) dated Sep. 6, 2017, corresponding to Eurasian Application No. 201590835/28; 2 total pages.
Eurasian Office Action (with English Translation) dated Sep. 6, 2017, corresponding to Eurasian Application No. 201590836/28; 2 total pages.
European Communication dated Aug. 2, 2017, corresponding to European Application No. 15 178 147.3; 8 pages.
Opekun, Jr. et al., "Lack of dose-response with Pancrease MT for the treatement of exocrine pancreatic insufficiency in adults," Blackwell Science Ltd., Aliment Pharmacol Ther (1997), vol. 11; pp. 981-986.
"Clinical Pharmacology and Biopharmaceutics Revew(s)", Center for Drug Evaluation and Research, Apr. 23, 2010, Application No. 022523Orig1s000; 37 pages—Retrieved from the Internet: https:www.accessdata.fda.gov/drugsatfda_docs/nda/2010/022523orig1s000clinpharmr.pdf.
"Pancrease MT Capsules", Aug. 2005, Drug Reference Encyclopedia; 7 pages—Retrieved from the Internet: https://theodora.com/drugs/pancrease_mt_capsules_mcneil_consumer.html.
European Communication dated Sep. 16, 2017, corresponding to European Application No. 14 815 008.9; 7 total pages.
Argentine Office Action dated Mar. 31, 2017, corresponding to Argentine Application No. P080100693; 6 pages (No English language translation available).
Taiwanese Office Action (with English translation), dated Feb. 16, 2017, corresponding to Taiwanese Aplication No. 102138934; 5 total pages.
Examination Report and Search Report issued by the Korean Intellectual Property Office dated Jul. 3, 2017, corresponding to AE Application No. UAE/P/0743/2009; 13 total pages.
Korean Office Action (with English Translation) dated Sep. 5, 2017, corresponding to Korean Application No. 10-2013-7010970; 12 total pages.
Japanese Office Action (with English translation) dated Mar. 27, 2018, corresponding to Japanese Application No. 2016-53356; 10 total pages.

(56) References Cited

OTHER PUBLICATIONS

Eiyogaku Zasshi (Nahomi Imaeda) "Food Compositition Table for Retort-Packaged Baby Foods", Department of Food Science and Nutrition, Faculty of Human Life and Environmental Sciences, Nagoya Women's University, Jpn. J. Nutr. Diet, 2008, vol. 66, No. 5; pp. 255-262.

Ensure Plus milkshake style, 2015 (online), [search Mar. 13, 2018], Retrived from the internet, URL: http://www.abbottnutrition.ie/content/datasheets/Ensure_Plus_datasheet_January_2015.pdf.

English translation of Russian Office Action and Search Report dated Feb. 16, 2018, corresponding to Russian Application No. 2016103606; 6 total pages.

European Examination Report dated Dec. 4, 2018, corresponding to European Application No. 14 859 866.7; 5 pages.

Singapore Search Report and Examination Report dated Feb. 9, 2018, corresponding to Singapore Application No. 10201405791X; 6 total pages.

Dominguez-Munoz et al., "Effect of Oral Pancreatic Enzyme Administration on Digestive Function in Healthy Subjects: Comparison Between Two Enzyme Preparations," Aliment Pharmacol Ther. 11, vol. 13, No. 2, Apr. 1, 1997; pp. 403-408.

Japanese Office Action dated Dec. 12, 2017, corresponding to Japanese Application No. 2016-196831; 3 total pages.

Chinese Office Action dated Jun. 2, 2017, corresponding to Chinese Application No. 201480027549.8; 7 pages.

Russian Office Action and Search Report (with English translation) dated Feb. 16, 2018, corresponding to Russian Application No. 2016103606; 13 total pages.

Russian Decision to Grant (with English translation), dated Feb. 27, 2018, corresponding to Russian Application No. 2015138541/15; 12 total pages.

Russian Office Action and Search Report (with English translation), dated Nov. 9, 2017, corresponding to Russian Application No. 2015138541/15; 17 total pages.

Australian Examination Report dated Jan. 8, 2018, corresponding to Australian Application No. 2014229330; 4 pages.

English translation of Japanese Office Action dated Feb. 27, 2018, corresponding to Japanese Application No. 2016-528615; 13 pages.

Korean Notice of Allowance (with English translation), dated Dec. 6, 2017, corresponding to Korean Application No. 10-2015-7004820; 3 pages.

Australian Examination Report dated Oct. 11, 2017, corresponding to Australian Application No. 2016204414; 3 pages.

Singapore Notice of Eligibility for Grant, including Examination Report and Search Report, dated Feb. 27, 2018, corresponding to Singapore Application No. 10201405791X; 9 total pages.

Indian Examination Report dated Dec. 29, 2017, corresponding to Indian Application No. 3078/CHENP/2013; 5 pages.

English translation of Korean Office Action dated Mar. 29, 2018, corresponding to Korean Application No. 10-2013-7010970; 3 pages.

Russian Office Action and Search Report (with English translation) dated Nov. 9, 2017, corresponding to Russian Application No. 2015138541; 11 total pegs.

English Translation of Japanese Office Action dated Nov. 6, 2017, corresponding to Japanese Application No. 2015-562502; 5 pages.

European Communication dated Dec. 4, 2017, corresponding to European Application No. 14859866.7; 5 pages.

Japanese Office Action (wish English translation), dated Nov. 14, 2017, corresponding to Japanese Application No. 2015-562502; 10 total pages.

European Communication dated Mar. 5, 2018, corresponding to counterpart European Application No. 15 750 805.2; 5 pages.

Solvay Pharmaceuticals: "Solvay Pharmaceuticals Creon (Pancrelipase Delayed-Release Capsules) Antiviral Drugs Advisory Committee, Dec. 2, 2008, Open Session (Appendices 1 and 2 for Closed Session under separate cover) Available for Public Disclosure Without Redaction"; Dec. 2, 2008 (XP055454900); Retrieved from the Internet: https://www.fda.gov/ohrms/dockets/ac/08/briefing/2008-4402b1-03-SOLVAY.pdf; 137 pages.

Canadian Office Action and Examination Search Report, dated Apr. 27, 2018 corresponding to counterpart Canadian Application No. 2,843,556; 6 total pages.

European Communication dated Jul. 19, 2018 and Issued in corresponding European Patent Application No. 14833670.4, 6 pages.

Notice of Opposition to a European Patent, European Patent No. EP2621476, dated Apr. 29, 2018 and related opposition documents; 1059 total pages.

Russian Search Report (with English translation) dated Sep. 10, 2018, corresponding to Russian Application No. 2015155470/15; 4 total pages.

Japanese Office Action (English translation) dated Aug. 28, 2018, corresponding to Japanese Application No. 2016-552457; 12 pages.

European Communication dated Sep. 13, 2018, corresponding to European Application No. 14 859 866.7; 6 pages.

Chinese third Office Action dated Aug. 20, 2018, corresponding to Chinese Application No. 2014800275498; 6 pages.

Otilia May Yue Koo, et al., "The Influence of Microcrystalline Cellulose Grade on Shape and Shape Distributions of Pellets Produced by Extrusion-Spheronization," Chem. Pharm. Bull., Nov. 2001, vol. 49, No. 11, pp. 1383-1387.

Citation cited in Notice of Oppoisition dated Nov. 8, 2017, corresponding to European Application No. EP14176579.2, Mannitol, pp. 424-428.

Citation cited in Notice of Oppoisition dated Nov. 8, 2017, corresponding to European Application No. EP14176579.2, FMC BioPolymer, the Science of Fomulation, Product information brochure for Avicel PH, (21 total pages).

Armstrong et al., Handbook of Pharmaceutical Excipients, Sixh Edition, Feb. 5, 2009, Edited by Raymond C. Rowe, et al., Cellulose, Microcrystalline; pp. 129-133.

Citation cited in Notice of Oppoisition dated Nov. 8, 2017 corresponding to European Application No. 14176579.2); Product Information leaflet (59755) for Arbocel BC200, Kremer Pigmente; 1 page.

Citation cited in Notice of Oppoisition dated Nov. 8, 2017 corresponding to European Application No. 14176579.2); Product Information leaflet for EXPLOTAB—Sodium Starch Glycolate from JRS Pharma—Product Desciption and Details, American Pharmaceutical Review, 2 pages.

Notice of Oppoisition to European Patent No. EP2818160 (European Application No. 14176579.2), dated Nov. 8, 2017; 35 total pages.

Van de Vijver, et al., Treatment of Infants and Toddlers With Cystic Fibrosis-related Pancreatic Insufficiency and Fat Malaborption With Pancrelipase MT, Original Article: Gastroenterology, JPGN, Jul. 2011, vol. 53, No. 1, pp. 61-64.

JP Office Action and English Translation issued for JP Application No. 2016-533356, dated Dec. 4, 2018, 14 pages.

English Translation of JP Patent Application 2011-093845, 11 pages.

AU Examination Report No. 1 for AU Patent Application No. 2014306222, dated Jan. 31, 2019, 4 pages.

IN Examination Report issued for IN Patent Application No. 201627004204, dated Feb. 25, 2019, 8 pages.

EP Communication with extended search report, EP Application No. 19215631.3, dated Feb. 21, 2020, 9 pages.

\* cited by examiner

DIGESTIVE ENZYME COMPOSITION SUITABLE FOR ENTERAL ADMINISTRATION

CROSS-RELATED APPLICATION

This application is a national phase entry of PCT/US2014/049569 filed Aug. 4, 2014. This application claims the benefit of PCT/US2014/049569 filed Aug. 4, 2014, which claims the benefit under 35 USC § 119(e) of U.S. Provisional Patent Application Ser. No. 61/864,314, filed Aug. 9, 2013. The disclosures of all of the above mentioned applications are herein incorporated by reference in their entirety for all purposes.

FIELD OF THE INVENTION

The present invention is directed to a digestive enzyme composition comprising an enterically coated digestive enzyme product, administrable nutritional medium, and a pharmaceutically acceptable low viscosity oily ingredient. The process for the preparation of the digestive enzyme composition comprises adding an enterically coated digestive enzyme product to an administrable nutritional medium and pharmaceutically acceptable low viscosity oily ingredient. The invention further provides a method for treating a patient suffering from exocrine pancreatic insufficiency related condition comprising administering to the patient a therapeutically effective dose of the digestive enzyme composition by means of a feeding tube.

BACKGROUND

The proper dosing of medications for patients is an important concern within the medical field. For infants, smaller children, and geriatric patients in particular, as well as sometimes also in adult populations, the administration of medications and dosing methods often present substantial issues. As is well known in the art, medications are provided in many forms (e.g., liquid, solid, and combinations of solids in liquids) and are delivered to patients in many ways (e.g., orally, via injection, transdermally). Nevertheless, there is still a need to optimize pancreatic enzyme supplement dosage formulations to improve both their efficacy and patient compliance in their use. Thus, for patients suffering from exocrine pancreatic insufficiency (EPI) what is in question is how to get a pancreatic enzyme supplement to be the most efficacious at the lowest dose, and have a well-defined safety profile.

In cases of exocrine pancreatic insufficiency (EPI), of which the FDA estimates more than 200,000 Americans suffer, involves a physiological disorder wherein individuals are incapable of properly digesting food due to a lack of digestive enzymes made by their pancreas. This loss of digestive enzymes leads to disorders such as the maldigestion and malabsorption of nutrients, which lead to malnutrition and other consequent and undesirable physiological conditions associated therewith. These disorders are common for those suffering from cystic fibrosis (CF) and other conditions which compromise the exocrine function of the pancreas, such as pancreatic cancer, pancreatectomy, and pancreatitis. The malnutrition can be life threatening if left untreated, particularly in the case of infants and CF patients. The disorder can lead to impaired growth, a compromised immune response, and shortened life expectancy.

Digestive enzymes, such as pancrelipase enzymes and other pancreatic enzyme products (PEPs) can be administered to at least partially remedy EPI. The administered digestive enzymes allow patients to more effectively digest their food.

The pancrelipase enzymes used for treating EPI are mainly a combination of three enzyme classes: lipase, amylase, and protease, together other enzymes including elastases, phospholipases, and cholesterases, amongst others, and various co-factors and coenzymes with their various co-factors and co-enzymes; the levels or potency in enzyme products are listed. These enzymes are produced naturally in the pancreas and are important in the digestion of fats, proteins and carbohydrates. The enzymes catalyze the hydrolysis of fats into glycerol and fatty acids, starch into dextrin and sugars, and proteins into amino acids and derived substances. However, digestion is a complex process involving many other enzymes and substrates that contribute to correct digestive functioning and in producing the full range of digestive products.

Pancrelipase enzymes are typically prepared from porcine pancreatic glands. Other pancrelipase sources include bovine pancreatic glands or pancreatic juices. The natural mammalian source of these enzymes results in a product with an enzyme composition which is similar to that secreted by the human pancreas. Other non-mammalian sources can also be used for example those described in U.S. Pat. No. 6,051,220, U.S. 2004/0057944, U.S. 2001/0046493, and WO2006044529.

Pancreatic enzymes show optimal activity under near neutral and slightly alkaline conditions. Under gastric conditions, pancreatic enzymes may be inactivated with a resulting loss in biological activity. Pancreatic lipases, which are important in the treatment of malabsorption, are especially sensitive to gastric inactivation. Thus, lipase activity is typically monitored to determine the stability of an enzyme composition containing lipase.

Composition containing digestive enzymes, such as pancrelipase enzymes, have been developed for oral administration in form of capsules (Zenpep®, Creon®) tablets (Viokace™, Viokase®) and granulate. However, if a patient is unable to swallow the capsules, each capsule can be opened and the contents sprinkled on a small amount of food, usually a soft, acidic food (such as commercially available applesauce) and administered orally to the patient with a spoon. Alternatively such medications may be administered orally for infants and children, using a syringe device containing the contents suspended in a medium amenable to administration thereby.

It is also recognized that for some patients, including pediatric and adult patients with an EPI related condition, feeding through enteral tubes, including smaller lumen enteral feeding tubes, such as gastric and jejunal feeding tubes, is required, more particularly for patients who are unable to take digestive enzymes orally.

Enteral feeding can be given through: the mouth (orogastric tube or OG); the nose (nasogastric tube or NG); the stomach (gastrostomy or GT); the intestine (jejunostomy or JT). They can be used to deliver calories and nutrients while sleeping at night or during the daytime. A nasogastric feeding tube, or "NG-tube," is passed through the nose, down the esophagus and into the stomach. Gastric feeding tubes, or "G-tube," on the other hand, are inserted through a small incision in the abdomen directly into the stomach, and are increasingly becoming the standard care for many patients, such as cystic fibrosis patients who exhibit chronic weight loss and require long-term enteral nutrition. Placement of a feeding tube is contingent upon a variety of conditions, including the overall patient health and age, severity of the condition, duration of placement, type of tube, means of placement, patient comfort, mitigating complications, potential for infection, financial considerations, availability, access and use. Thus, a variety of tubes are available in a number of sizes for such applications.

Short-term benefits of enteral feeding include immediate weight gain and increased energy. Long term gains include an increase in body fat, lean muscle mass, improved strength, a stronger immune system, less weight loss during pulmonary infections, a greater sense of control over body weight and numerous other benefits.

However, for enteral administering of digestive enzymes in particulate form, even when added with an administrable nutritional medium, there are preparative and administrative issues therewith. One issue is how to ensure that the digestive enzymes can effectively exert their enzyme activity on constituents susceptible thereto in an administrable nutritional medium when administered in a mixture therewith, and in obviating obstructions to the enteral tube by the digestive enzyme particulates. Use of tablet forms of digestive enzyme products also suffers for the same reasons. It is also mandatory to have available stable and homogenous composition to ensure consistent and complete delivery of the digestive enzymes by enteral administration, e.g., through a syringe outlet and through the lumen of the G-tube, without clogging, or sticking. Such administration procedure is affected by several factors, in particular, by the amount of digestive enzymes, dimension and shape of enzymes particles. Administrable nutritional medium, tube characteristics (internal diameter), digestive enzyme composition preparation and delivery procedure are also important factors.

To avoid problems during enteral administration, low dosage strengths are usually preferred over high strengths. Scalability is not considered and the proposed protocols are preferably aimed at administering pancrelipase particles with baby food using the smallest diameter and longest stoma length of tubes (the internal diameter and length of the tube). In fact, only low dose enzyme capsules are recommended for administration with feeding tubes. The dose of 4,000 IU USP lipase (Pancrecarb® MS4) is administered in combination with applesauce through G-tubes using 14 Fr feeding tubes. The content of a 12,000 lipase units capsule of Creon® is reported to be administered through G-tubes of size 16 Fr or 18 Fr (depending on the tube types) after admixing it to 15 mL of high viscosity medium (Shlieout et al, Clin Drug Investig, 31, 7, e1-e7, 2011). In some pancrelipase products the dimension/shape and/or amount of the beads does not allow a proper enteral administration. Clogging of tube still remains a big problem in the enteral administration which is not acceptable therapeutically.

The administration of high dosage strengths using feeding tubes with suitable diameter is not reported because the scalability of the above low dosage strengths is problematic. Avoiding the risk of feeding tube blockage (sticking, clogging/obstruction) and damage of the pellets (pellet integrity is important to ensure gastroresistance and lipase activity) are problems that have not been solved for beads having larger or non-uniform dimensions, or having broad particle size range.

In view of the aforesaid, there is no quick, practical, and effective process for enterally administering a digestive enzyme product that can be applied by different people and with different equipments. Furthermore, there is no protocol that is suitable for enterally administrating high dosage strengths of the digestive enzymes of particles with large dimension by enteral administration without any active ingredient damage and without obstruction of the enteral feeding tube.

SUMMARY OF THE INVENTION

The present invention is directed to a digestive enzyme composition comprising an enterically coated digestive enzyme product, administrable nutritional medium, and a pharmaceutically acceptable low viscosity oily ingredient. The process for the preparation of the digestive enzyme composition comprises adding an enterically coated digestive enzyme product to an administrable nutritional medium and pharmaceutically acceptable low viscosity oily ingredient. The invention further provides a method for treating a patient suffering from exocrine pancreatic insufficiency related condition comprising administering to the patient a therapeutically effective dose of the digestive enzyme composition by means of a feeding tube administrable nutritional medium.

According to an aspect of the invention, the digestive enzyme composition includes an enterically coated digestive enzyme product, administrable nutritional medium, a pharmaceutically acceptable low viscosity oily ingredient. In one embodiment, the enterically coated digestive enzyme product has an enteric polymer layer. In one embodiment, the enterically coated digestive enzyme is an enterically coated pancrelipase product. In one embodiment, the enterically coated pancrelipase product is a multiparticulated product. The multiparticulated product is in the form of beads, powder, granules, tablets, spheres, minitablets, microtablets, microparticles, microspheres, microcapsules or micropellets.

In one embodiment, the enteric polymer is selected from the group consisting of cellulose acetate phthalate, hydroxypropyl-methylcellulose phthalate, hydroxypropyl-methylcellulose acetate succinate, shellac, methylmethacrylate copolymer, and methacrylic acid/methylmethacrylate copolymer, and methacrylic acid-ethyl acrylate copolymer (1:1). In one embodiment, the digestive enzyme product is in therapeutically effective amount.

In one embodiment, the administrable nutritional medium is an administrable nutritional medium, a nutritional formula, a soft food. In another embodiment, the administrable nutritional medium is a baby food.

In one embodiment, the low viscosity oily ingredient is selected from the group consisting of vegetable oils, synthetic oils, and fatty acids, or mixture thereof. The vegetable oil is selected from the group consisting of sunflower oil, olive oil, extra virgin olive oil, wheat germ oil, codliver oil, borage oil, sesame oil, soybean oil, arachis oil, corn oil, cottonseed oil, linseed oil, coconut oil, rapeseed oil, sesame oil, peanut oil, safflower oil, sweet almond oil, and apricot kernel oil, or mixture thereof.

In one embodiment, the soft food is added in amount of about 2 mL to about 20 mL per each about 5,000 to about 20,000 lipase IU USP of pancrelipase product. In another embodiment, the soft food is added in amount of about 5 mL to about 10 mL per each about 5,000 to about 20,000 lipase IU USP lipase of pancrelipase particles. In one embodiment, the low viscosity oily ingredient is added in amount of about 5% to about 25% volume/volume of administrable nutritional medium.

According to another aspect of the invention, a process for the preparation of the digestive enzyme composition is provided. The process includes mixing the enterically coated digestive enzyme product, administrable nutritional medium, pharmaceutically acceptable low viscosity oily ingredient. The enterically coated digestive enzyme product, administrable nutritional medium, and low viscosity oily ingredient are either sequentially added and mixed in a container and then the composition is poured in a syringe, or they are partially added and mixed in a container, partially added in a syringe and then they admixed together in the syringe, or they are added directly in a syringe and mixed herein. The process further includes the steps of: 1) adding enterically coated pancrelipase particles into a container; 2) placing an administrable nutritional medium in a syringe barrel followed by the pancrelipase particles and then a low viscosity oily ingredient; 3) shaking the syringe up and down vigorously to disperse the pancrelipase particles in the obtained composition; and 4) eliminating excess of air from syringe.

The process further includes the steps of 1) placing an administrable nutritional medium in a syringe; 2) adding enterically coated pancrelipase particles thereto; 3) adding the low viscosity oily ingredient thereto; 4) shaking the syringe to disperse the pancrelipase particles in the obtained composition; and 5) eliminating excess of air from syringe.

According to yet another aspect of the invention, a method of treating a pediatric or adult patient in need of the digestive enzyme composition is provided. The method includes enterally administering to the patient the digestive enzyme composition including an enterically coated digestive enzyme product, administrable nutritional medium, a pharmaceutically acceptable low viscosity oily ingredient.

In one embodiment, the digestive enzyme product is an enterically coated pancrelipase product in a therapeutically effective amount of about 5,000 IU USP lipase or greater, administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube used for the enteral administration has internal diameter of at least about 18 Fr.

In one embodiment, the digestive enzyme product is an enterically coated pancrelipase product in a therapeutically effective amount of about 10,000 IU USP lipase or greater, the administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube used for the enteral administration has internal diameter of at least about 18 Fr.

In one embodiment, the administrable nutritional medium is soft food and the low viscosity oily ingredient is vegetable oil. In another embodiment, the administrable nutritional medium is baby food and the low viscosity oily ingredient is sunflower seed oil.

DETAILED DESCRIPTION

One embodiment of the invention is a digestive enzyme product that is an enterically coated pancrelipase product.

Another embodiment of the invention is the enterically coated digestive enzyme product in a multiparticulate form.

The invention establishes a reliable procedure for a direct administration of enterically coated pancrelipase particles in presence of different administrable nutritional media through an appropriate syringe and a tube of suitable size and type, to ensure consistent and complete delivery of the pancrelipase beads through the syringe outlet and through the lumen of the tube without clogging, sticking, and without beads damage or loss of enteric coating integrity.

Multiparticulates may be in the form of beads, powder, granules, tablets, spheres, minitablets, microtablets, microparticles, microspheres, microcapsules or micropellets. The digestive enzyme product used according to the invention may be in any suitable dosage forms including tablets, capsules, granules, or sachets.

The digestive enzyme product useful according to the invention contains enterically coated pancrelipase enzyme particles.

The term enterically coated identifies the presence of an enteric polymeric layer around the enzyme particles. An enteric polymer is a polymer that protects the digestive enzymes from the gastric environment. Examples of enteric polymers or pH-dependent water soluble polymers are cellulose acetate phthalate, hydroxypropylmethylcellulose phthalate, hydroxypropylmethylcellulose acetate succinate, and shellac, methylmethacrylate copolymers, and methacrylic acid/methylmethacrylate copolymers, methacrylic acid-ethyl acrylate copolymer (1:1) (such as Eudragit® L30D55).

Examples of such enterically coated pancrelipase enzyme products available on the market include Zenpep® and Ultresa®.

The term "digestive enzyme" used herein denotes an enzyme in the alimentary tract which breaks down the components of food so that they can be taken or absorbed by the organism. Non-limiting examples of digestive enzymes include pancrelipase enzymes (also referred to as pancrelipase or pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-galactosidase, lactase, sucrase, isomaltase, and mixtures thereof.

The term "pancreatic enzyme" as used herein refers to any one of the enzyme types present in the pancreatic secretion, such as amylase, lipase, protease, or mixtures thereof, or any extractive of pancreatic origin having enzymatic activity, such as pancreatin.

The terms "pancrelipase enzymes" or "pancrelipase" or "pancreatin" denotes a mixture of several types of enzymes, including amylase, lipase, and protease enzymes. Pancrelipase enzyme is commercially available, for example from Nordmark Arzneimittel GmbH, or Scientific Protein Laboratories LLC.

The term "API" is used herein to denote "digestive enzymes" or "pancrelipase enzymes" or "pancreatin" or "pancrelipase".

The term "lipase" denotes an enzyme that catalyzes the hydrolysis of lipids to glycerol and simple fatty acids. Examples of lipases suitable for the present invention include, but are not limited to animal lipase (e.g., porcine lipase), bacterial lipase (e.g., *Pseudomonas* lipase and/or *Burkholderia* lipase), fungal lipase, plant lipase, recombinant lipase (e.g., produced via recombinant DNA technology by a suitable host cell, selected from any one of bacteria, yeast, fungi, plant, insect or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), synthetic lipase, chemically-modified lipase, and mixtures thereof. The term "lipids" broadly includes naturally occurring molecules including fats, waxes, sterols, fat-soluble vitamins (such as vitamins A, D, E and K), monoglycerides, diglycerides, triglycerides, phospholipids, etc.

The term "amylase" refers to glycoside hydrolase enzymes that break down starch, for example α-amylases, β-amylases, γ-amylases, acid α-glucosidases, salivary amylases such as ptyalin, etc. Amylases suitable for use in the present invention include, but are not limited to animal amylases, bacterial amylases, fungal amylases (e.g., *Aspergillus* amylase, for example, *Aspergillus oryzae* amylase), plant amylases, recombinant amylases (e.g., produced via recombinant DNA technology by a suitable host cell, selected from any one of bacteria, yeast, fungi, plant, insect or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, and mixtures thereof.

The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism. Non-limiting examples of proteases suitable for use in the present invention include serine proteases, threonine proteases, cysteine proteases, aspartic acid proteases (e.g., plasmepsin) metalloproteases and glutamic acid proteases. In addition, proteases suitable for use in the present invention include, but are not limited to animal proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases, which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, and mixtures thereof.

The pancrelipase enzymes of the composition of present invention can include one or more lipases (i.e., one lipase, or two or more lipases), one or more amylases (i.e., one amylase, or two or more amylases), one or more proteases (i.e., one protease, or two or more proteases), and is mixtures of these enzymes in different combinations and ratios.

Lipase activities in the compositions useful for the present invention can be from about 650 to about 45,000 IU (USP method), from about 675 to about 825 IU, from about 2,500 to about 28,000 IU (USP method), from about 2,700 to about 3,300 IU, from about 4,500 to about 5,500 IU, from about 8,000 to about 11,000 IU, from about 13,500 to about 16,500 IU, and from about 18,000 to about 22,000 IU, from about 22,500 to about 27,500 IU, from about 36,000 to about 44,000 IU, and all ranges and sub-ranges there between. Also the lipase activity can range from about 5,000 PhEur lipase units to about 30,000 PhEur lipase units, it may be about 5,000, or about 10,000, or about 12,500, about 15,000 or about 20,000 or about 30,000, or about 40,000 PhEur lipase units.

Amylase activities in the compositions can be from about 1,600 to about 6,575 IU (USP), from about 6,000 to about 225,000 IU, for example from about 6,400 to about 26,300 IU, from about 10,700 to about 43,800 IU, from about 21,500 to about 87,500 IU, from about 32,100 to about 131,300 IU, from about 42,900 to about 175,000 IU, from about 53,600 to about 218,700 IU and all ranges and sub-ranges there between.

The protease activities in the compositions can be from about 1,250 to about 3,850 IU (USP), from about 5,000 to about 130,000 IU, for example from about 5,000 to about 15,400 IU, from about 8,400 to about 25,700 IU, from about 16,800 to about 51,300 IU, from about 25,000 to about 77,000 IU, from about 33,500 to about 102,800 IU, from about 41,800 IU to about 128,300 IU and all ranges and sub-ranges there between.

The lipase activity can range from about 675 to about 825 IU (USP), the amylase activity from about 1,600 to about 6,575 IU, and the protease activity from about 1,250 to about 3,850 IU (USP). The lipase activity can range from about 2,700 to about 3,300 IU, the amylase activity from about 6,400 to about 26,300 IU, and the protease activity from about 5,000 to about 15,400 IU (USP). The lipase activity can range from about 4,500 to about 5,500 IU, the amylase activity from about 10,700 to about 43,800 IU, and the protease activity from about 8,400 to about 25,700 IU (USP). The lipase activity can range from about 9,000 to about 11,000 IU, the amylase activity from about 21,500 to about 87,500 IU, and the protease activity from about 16,800 to about 51,300 IU (USP). The lipase activity from about 13,500 to about 16,500 IU, the amylase activity from about 32,100 to about 131,300 IU, and the protease activity from about 25,000 to about 77,000 IU (USP). The lipase activity can range from about 18,000 to about 22,000 IU, the amylase activity from about 42,900 to about 175,000 IU, and the protease activity from about 33,500 to about 102,600 IU (USP). The lipase activity can range from about 22,000 to about 27,500 IU, the amylase activity from about 53,600 to about 218,700 IU, and the protease activity from about 41,800 IU to about 128,300 IU (USP).

In one embodiment of the present invention single units containing a fraction of the above listed activities can be used. In the invention an effective amount of pancrelipase enzymes is used to prepare the composition, said effective amount of enzymes may be of a total of about 3,000, about 4,000, about 4,200, about 5,000, about 6,000, about 8000, about 10,000, about 10,440, about 10,500, about 13,800, about 15,000, about 16,000, about 16,800, 16,800, about 20,000, about 20,880, about 21,000, about 24,000, or 25,000, IU (USP), lipase units or multiple thereof, or about 5,000, or about 12,500, or about 30,000 PhEur lipase units or multiple thereof.

One embodiment of the invention is a digestive enzyme composition comprising enterically coated pancrelipase particles, administrable nutritional medium, and a pharmaceutically acceptable low viscosity oily ingredient.

Another embodiment according to the invention is directed to administrable nutritional medium with high viscosity. Such can provide for the beads to be suspended properly, thereby guaranteeing passage through the entire G-tube to reach the intended site of action without sedimentation, which may lead to clogging of the tube.

Another embodiment according to the invention is the administrable nutritional medium that is slightly acidic. It has pH<5 to avoid potential disruption of the enteric coating, early release of enzymes and/or loss of enzyme activity. It is compatible with the digestive enzyme product. Its viscosity is suitable both to enable the suspension of pancrelipase particles and to ensure load and discharge from the syringe.

It is suitable for administration to all kind of patients including infants and young children and it does not affect the patency of G-tube.

The administrable nutritional medium according to the invention may be a nutritional formula or a soft food such as baby food.

The nutritional formula can be one that is suitable for adult or children or infant. It contains specific amount of nutrients, which are mixture of carbohydrates, lipids, proteins; polymeric components that may be in hydrolyzed form. The nutritional formula may further comprise other ingredients such as trace elements and fibers. Enteral formulas commonly used include polymeric or other specialized formulas. Polymeric formulas including milk-based or lactose-free commercial formulas are commercially available and generally provide a complete, balanced diet. Specialized formulas include hydrolyzed protein or sometimes amino acid formulas, which are used for patients who have difficulty digesting complex proteins.

Examples of commercial liquid adult/children enteral formula are Peptamen® Junior 1, Peptamen® Junior 1.5, Ensure® Plus. Examples of commercial infant formulas are Humana® 1, Neolatte® 1, and Neolatte® 2.

Soft food is a proper administrable nutritional medium. It presents the advantage that it is readily available on market and commonly used (particularly applesauce) for administering PERT (Pancreatic Enzyme Replacement Therapy) in infants and young children. Upon storage, the soft food should not separate into two or more phases (such as one upper liquid phase and one lower viscous phase). It should also be homogeneous, that is, it should not contain any small fruit (apple) pieces which could clog the G-tube viscosity, flowability and homogeneity are important characteristics. Soft food has high viscosity and is slightly acidic.

In one embodiment of the invention the administrable nutritional medium is soft food. In one embodiment according to the invention, soft food is present in amount of about 2 mL to about 20 mL (e.g., about 2, about 5, about 10, about 15 or about 20 mL) per each about 5,000 to about 20,000 lipase IU USP, more particularly about 2 mL to about 15 mL, further particularly about 2 mL to about 10 mL. In one embodiment of the invention soft food is present in amount of about 2 mL to about 15 mL (e.g., about 2, about 5, about 10, about 15 mL per each 20,000-40,000 lipase IU FIP).

Examples of soft foods are sauces based on fruit spread. Other examples of soft foods are selected from applesauce, applesauce $3^{rd}$ food, apple banana $3^{rd}$ food, peach $3^{rd}$ food, regular applesauce, banana sauce, banana $1^{st}$ food, pears $1^{st}$ food, applesauce $1^{st}$ food; apple, banana and peach $3^{rd}$ food.

The low viscosity oily ingredient is selected from the group of vegetable oils, synthetic oils, and fatty acid, or mixtures thereof.

The vegetable oil is selected from sunflower oil, olive oil, extra virgin olive oil, wheat germ oil, cod liver oil, borage oil, sesame oil, soybean oil, arachis oil, corn oil, cottonseed oil, linseed oil, coconut oil, rapeseed oil, sesame oil, peanut oil, safflower oil, sweet almond oil, and apricot kernel oil, or mixtures thereof.

Synthetic oil is selected from medium chain triglycerides (MCT), propylene glycol dicaprylocaprate, glyceryl behenate, glyceryl monolinoleate, glyceryl oleate, glyceryl caprylate/caprate, coco caprylate/caprate, glyceryl laurate, glyceryl myristate, glyceryl cocoate, butylene glycol dicaprylate/caprate hydrogenated vegetable oil, and refined vegetable oil, or mixture thereof.

The fatty acid is selected from C8-, C9-, C10-, C11-, C12-, C13-, C14-, C15-, C16-, C17-, C18-, C19-, C20-, C21-, and C22-fatty acid, or mixtures thereof.

The low viscosity oily ingredient is present together with the soft foods in an amount to ensure that suitable therapeutic dose strength is administered without any risks. The low viscosity oily ingredient is present in amount of about 1.2 mL to about 10 mL (about ¼ to about 1 teaspoon) per each about 5 mL of soft food. The preferred amount of low viscosity oily ingredient is about 1.2 mL to about 5 Ml, more particularly about 5 mL.

In one embodiment of the invention the low viscosity oily ingredient is a vegetable oil.

In a particular embodiment the vegetable oil is sunflower oil.

One embodiment of the invention, is the digestive enzyme composition wherein the enterically coated digestive enzyme product is a multiparticulate enterically coated pancrelipase product, the administrable nutritional medium is present in amount of about 2 mL to about 20 mL per each about 5,000 to about 20,000 lipase IU USP of the pancrelipase product, and the low viscosity oily ingredient is present in amount of about 5% to about 25% volume/volume of administrable nutritional medium.

Another embodiment of the invention, is the digestive enzyme composition wherein the enterically coated digestive enzyme product is a multiparticulate enterically coated pancrelipase product, the administrable nutritional medium is present in amount of about 10 mL to about 20 mL per each about 5,000 to about 20,000 lipase IU USP of the pancrelipase product, and the low viscosity oily ingredient is present in amount of about 5% to about 25% volume/volume of administrable nutritional medium.

Yet another embodiment of the invention, is the digestive enzyme composition wherein the enterically coated digestive enzyme product is a multiparticulate enterically coated pancrelipase product, the administrable nutritional medium is present in amount of about 2 mL to about 10 mL per each about 5,000 to about 20,000 lipase IU USP of the pancrelipase product, and the low viscosity oily ingredient is present in amount of about 5%, about 10%, about 20, or about 25% volume/volume of administrable nutritional medium.

A preferred particular embodiment of the invention, is the digestive enzyme composition wherein the enterically coated digestive enzyme product is a multiparticulate enterically coated pancrelipase product, the administrable nutritional medium is a soft food, (such as a baby food) in an amount of about 5 mL to about 10 mL per each about 5,000 to about 20,000 lipase IU USP of the pancrelipase product, and the low viscosity oily ingredient is a vegetable oil (such as sunflower seed oil) in amount of about 5%, about 10%, about 20%, or about 25% volume/volume of administrable nutritional medium.

Another embodiment of the invention is a process for the preparation of the digestive enzyme composition comprising mixing an enterically coated pancrelipase enzyme product, administrable nutritional medium and a low viscosity oily ingredient to obtain the digestive enzyme composition.

Yet another embodiment of the invention is a process for the preparation of the digestive enzyme composition wherein it is a homogeneous dispersion comprising mixing an enterically coated pancrelipase enzyme product, an administrable nutritional medium and a low viscosity oily ingredient to obtain the digestive enzyme composition as a homogeneous dispersion.

The process for preparing the digestive enzyme composition comprising multiparticulated enterically coated pancrelipase particles is conducted in no specific order for mixing the ingredients. Digestive enzyme product (such as pancrelipase particles) may be admixed with administrable nutritional medium, more particularly to form an homogeneous mixture, and then the low viscosity oily ingredient low is mixed therewith, or administrable nutritional medium is mixed with the low viscosity oily ingredient, more particularly to form an emulsion, and then digestive enzyme product (such as pancrelipase particles) are mixed therewith.

The amount of digestive enzyme composition delivered enterally through the syringe and tube is always constant independently of the addition order. In one embodiment of the invention the combining of the digestive enzyme composition ingredients and their mixing is performed in a separate cup or container and then the mixture can be administered enterally.

In another embodiment of the invention the combining of the digestive enzyme composition ingredients and their mixing are partially done partially (first step) in a separate cup or container and partially (second step) in the syringe. Then the mixture of first step is poured in the syringe and admixed together with the mixture of step 2 already prepared in the syringe.

In a further embodiment of the invention all the combining of the digestive enzyme composition ingredients and mixing steps are carried out directly in the syringe. Accordingly, the mixing steps are carried out manually or by vigorously shaking the syringe. In any case, it is important that during addition and mixing steps no dose loss occurs.

In one embodiment the preparation of the digestive enzyme composition of the invention comprises the following steps:

Method A: 1) Opening the dosage form containing the enterically coated pancrelipase particles (such as capsule) and pouring the beads into a container; 2) pouring the pancrelipase particles into the syringe barrel; 3) adding with aspiration an appropriate volume of administrable nutritional medium into a syringe; 4) adding by aspiration a low viscosity oily ingredient; and 5) covering the syringe tip (such as with the finger) and shaking the syringe to homogenize the composition.

Method B: 1) Placing an administrable nutritional medium into a container (such as a medicine cup or small bowl); 2) adding enterically coated pancrelipase particles into the administrable nutritional medium; 3) stirring manually the particles and administrable nutritional medium mixture, more particularly to obtain an homogeneous suspension; and 4) adding a low viscosity oily ingredient and stirring manually mixture to obtain the composition.

Method C: 1) Adding enterically coated pancrelipase particles into a container (such as small cup or bowl); 2) placing an administrable nutritional medium in a syringe barrel followed by the pancrelipase particles and then a low viscosity oily ingredient; 3) shaking the syringe up and down vigorously to disperse the pancrelipase particles in the obtained composition; and 4) eliminating excess of air from syringe.

More specifically method C comprises the following steps: 1) opening one dosage form of enterically coated pancrelipase product and pouring the pancrelipase particles into a container (such as small cup or bowl); 2) removing the plunger from the syringe, covering the syringe tip (such as with the finger) and placing administrable nutritional medium into the syringe barrel followed by the pancrelipase particles and then the low viscosity oily ingredient; 3) reattaching the plunger and tilting the syringe tip upward; 4) covering the tip (such as with the finger), shaking the syringe up and down vigorously to disperse the pancrelipase particles; and 5) eliminating excess of air from syringe.

Alternatively, the method C comprises the following steps: 1) placing an administrable nutritional medium in a syringe; 2) adding enterically coated pancrelipase particles thereto; 3) adding the low viscosity oily ingredient; 4) shaking the syringe to disperse the pancrelipase particles in the obtained composition; and 5) eliminating excess of air from syringe.

More specifically the alternative method C comprises the following steps: 1) removing the plunger from the syringe, covering the syringe tip and placing administrable nutritional medium into the syringe barrel; 2) adding the pancrelipase particles from one pancrelipase product; 3) adding the low viscosity oily ingredient; 4) reattaching the plunger and tilting the syringe tip upward; 5) covering the tip, shaking the syringe up and down vigorously to disperse the pancrelipase particles; and 6) eliminating excess of air from syringe.

In one embodiment of the process for preparing the digestive enzyme composition, the ingredients are added in the following sequential order: administrable nutritional medium, digestive enzyme product (e.g., enterically coated pancrelipase particles), and then low viscosity oily ingredient. The addition and mixing is preferably carried out directly in the syringe (method C). This method is a simple and easily reproducible and the risk of dose loss is very reduced.

The homogeneous dispersion of pancrelipase enzymes in the administrable nutritional medium and the low viscosity oily ingredient is a stable composition, wherein the enzymes retain their activity and there is no enzyme degradation occurring during the administration.

This pancrelipase enzyme is used for nutritional management of impaired gastrointestinal function in pediatric and adults patients and is suitable to be administered via a syringe into a feeding G-tube without markedly evident phase separation for the administration period. A broad range of pancrelipase products having different dosage strengths and particle size dimension and shape can be used with this approach.

The digestive enzyme composition of the invention comprising an enterically coated pancrelipase product, administrable nutritional medium and a pharmaceutically acceptable low viscosity oily ingredient is suitable for administration to infants, children, adults, aged patients, or other patients suffering from EPI, which allows medication to be dispensed carefully and with controlled dosing.

The present invention also encompasses a method of enteral administration to pediatric or adult patients of the digestive enzyme composition of the present invention. It comprises preparing the composition as described above (either in the syringe directly or in a separate container followed by pouring it into the syringe barrel) and then injecting the composition (enzyme particles and administrable nutritional medium and low viscosity oily ingredient) with a steady push until the entire mixture is delivered in the feeding tube. After injection, an appropriate volume of administrable nutritional medium (such as the same volume of administrable nutritional medium) or water may be further used to "wash" the tube and make sure that all pancrelipase beads are flushed and the total dose is administered. This method comprises the steps of 1) mixing an enterically coated pancrelipase product, administrable nutritional medium, and an low viscosity oily ingredient, either by adding and mixing these ingredients in a container followed by pouring it into a syringe or by adding and mixing these ingredients directly in a syringe; 2) injecting the pancrelipase composition (enzymes particles and administrable nutritional medium and low viscosity oily ingredient) from the syringe with a steady push in the feeding tube; and 3) flushing the syringe and tube with administrable nutritional medium or water.

In one embodiment of the method of administration according to the invention, the composition comprises an enterically coated pancrelipase product (which is multiparticulated), an administrable nutritional medium and a low viscosity oily ingredient, wherein the pancrelipase product is in therapeutically effective amount of about 5,000 IU USP lipase or greater, the administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube has internal diameter of about 18 Fr or higher.

In one embodiment of the method of administration according to the invention, the digestive enzyme composition comprises an enterically coated pancrelipase product (which is multiparticulated), an administrable nutritional medium and a low viscosity oily ingredient, wherein the pancrelipase product is present in therapeutically effective amount of about 10,000 IU USP lipase or greater (higher enzymatic activity), the administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube has internal diameter of about 18 Fr or higher.

In another embodiment of the method of administration according to the invention, the digestive enzyme composition comprises an enterically coated pancrelipase product (which is multiparticulated), an administrable nutritional medium and a low viscosity oily ingredient, wherein the pancrelipase product is in therapeutically effective amount of about 5,000 IU USP lipase or greater (more lipase units), the administrable nutritional medium is present in amount of about 2 mL to about 10 mL per each about 5,000 to about 20,000 lipase IU USP of the pancrelipase product, the low viscosity oily ingredient is present in amount of about 5%, about 10% or about 25% volume/volume of administrable nutritional medium, and the G-tube has internal diameter of about 18 Fr or higher.

In another embodiment of the method of administration according to the invention, the digestive enzyme composition comprises an enterically coated pancrelipase product (which is multiparticulated), an administrable nutritional medium and an low viscosity oily ingredient, wherein the pancrelipase product is in therapeutically effective amount of about 10,000 IU USP lipase or greater, the administrable nutritional medium is present in amount of about 2 mL to about 10 mL per each about 5,000 to about 20,000 lipase IU USP of the pancrelipase product, the low viscosity oily ingredient is present in amount of about 5%, about 10% or about 25% volume/volume of administrable nutritional medium, and the G-tube has internal diameter of about 18 Fr or higher.

In another embodiment of the method of administration according to the invention, the digestive enzyme composition comprises an enterically coated pancrelipase product (which is multiparticulated), a soft food (such as a baby food) and a vegetable oil (such as sunflower seed oil), wherein the pancrelipase product is in therapeutically effective amount of about 5,000 IU USP lipase or greater, the soft food is present in amount of about 2 mL to about 10 mL per each about 5,000 to about 20,000 lipase IU USP of the pancrelipase product, the vegetable oil is present in amount of about 5%, about 10% or about 25% volume/volume of administrable nutritional medium, and the G-tube has internal diameter of about 18 Fr or higher.

In another embodiment of the method of administration according to the invention, the composition comprises an enterically coated pancrelipase product (which is multiparticulated), a soft food (such as a baby food) and a vegetable oil (such as sunflower seed oil), wherein the pancrelipase product is in therapeutically effective amount of above about 10,000 IU USP lipase, the soft food is present in amount of about 2 mL to about 10 mL per each about 5,000 to about 20,000 lipase IU USP of the pancrelipase product, the vegetable oil is present in amount of about 5%, about 10% or about 25% volume/volume of administrable nutritional medium, and the G-tube has internal diameter of about 18 Fr or higher.

The present invention describes a reliable procedure suitable for the administration of a enterically coated pancrelipase particles through a gastrostomy-tube or nasogastric-tube and ensure consistent delivery of the dose through the lumen of the tube without clogging, sticking and preserving the tube patency. Administration is conducted through different tubes that are chosen according to patients, from newborns, to pediatric, to adult patients. The successful testing of the diameter sizes shown herein indicates that the use of diameter tube of different type and/or different manufacturer is feasible when using the described administration procedure.

With the process of the instant invention, the digestive enzyme composition comprising an enterically coated pancrelipase product, administrable nutritional medium, and a low viscosity oily ingredient is very stable with regards to the enzymatic activity.

From the foregoing description and the experimental part, it can be seen that the present invention provides several important advantages. The invention provides a simple and fast process for complete administration of a therapeutic dose of multiparticulated pancrelipase product by means of a calibrated tube. It obviates clogging of tubes during administering of the digestive enzyme composition, sticking of the digestive enzyme composition during the administration, damage or loss of enteric coating integrity of the digestive enzyme product component in the digestive enzyme composition occurs during administration with such process. The lipase activity is maintained after addition of pancrelipase enzymes into the administrable nutritional medium and remains stable in the composition and the lipolysis is effectively achieved.

Experimental

Materials

Pancrelipase enzymes products: microtablets Zenpep® 5,000 IU USP lipase/cps (dimension: 94.8% has >1.18 mm, <2.36 mm); minitablets Zenpep® 10,000 IU USP lipase/cps; microtablets Zenpep® 10,000 IU USP lipase/cps; Kreon® 40,000 IU FIP lipase/cps and Creon® 24,000 IU USP lipase/cps Panzytrat® 40,000 IU FIP lipase/cps; minitablets Ultresa® 13,800 IU USP lipase/cps (dimensions: about 2.0 mm×2.0 mm).

Administrable nutritional media: Applesauce (Beech-Nut), Applesauce $3^{rd}$ Food (Gerber®), Apple Banana $3^{rd}$ Food (Gerber®) Peach $3^{rd}$ Food (Gerber®) Regular Applesauce (Mott's®); Banana (Beech-Nut); Granny Smith flavoured Applesauce (Mott's®); Banana $1^{st}$ Food (Gerber®) Pears $1^{st}$ Food (Gerber®); Applesauce 1st Food (Gerber®); Apple, Banana and Peach $3^{rd}$ Food (Gerber®). Applesauce (Beech-Nut), Applesauce 3rd Food (Gerber®), Apple, Banana and Peach $3^{rd}$ Food (Gerber®), Banana $3^{rd}$ Food (Gerber®) have medium viscosity, very high homogeneity, and very high flowability. Applesauce (Beech-Nut), Banana (Beech-Nut), Banana $1^{st}$ Food (Gerber®), Pears $1^{st}$ Food (Gerber®), Applesauce 1st Food (Gerber®) have high viscosity, very high homogeneity, and high flowability. Regular Applesauce (Mott's®), Banana (Beech-Nut); Granny Smith flavoured Applesauce (Mott's®) have very high viscosity, medium homogeneity, with coarse fruit residues and medium flowability.

Low viscosity oily ingredients: sunflower oil, extra virgin olive oil, or rapeseed oil.

Methods

Lipolytic activity. Measurement is carried out with a method based on the compendia procedure of lipase assay described in the pancrelipase enzymes USP monograph, which is based on the titration, by means of pH-stat method, of the free fatty acids formed from the hydrolysis of esterified fatty acids in the substrate used (olive oil). It is based on the following principle: lipase catalyses the hydrolysis of the triglycerides which leads to the formation of free fatty acids (FFA). The titration of the formed FFA according to time provides for the determination of the enzymatic activity of lipase, which can be expressed in units: 1 U=1 µmole of formed FFA per minute. The reaction occurs by maintaining a steady pH value through an experimental system that provides for the addition of NaOH (titrant) when the pH value changes compared to a fixed value (pHstat method). The quantity of added titrant according to time corresponds to the quantity of FFA formed by the lipase action on the triglycerides. The curve slope {added titrant=f (volume (mL)/time (minutes))} gives the lipase enzymatic activity.

Dissolution tests is performed using two stages dissolution: 1 h acid stage in 800 mL pH 1.2 buffer without enzyme and 30 minutes in 800 mL pH 6.0 buffer, the theoretical lipase concentration is equal to 14 IU USP/mL. Lipase activity is measured with the above test.

Assessment of sample preparation procedure comprises the following the tests:
- evaluation of clogging, sticking of G-tubes is performed by visual observation.
- evaluation of patency is performed by verifying the absence of residual of pancrelipase particles and the completeness of injected material recovery by visual inspection.
- evaluation offlow rate is performed by recording the time needed for bolus to pass through the entire tube after applying a steady pressure to the plunger which is compared with blank.
- delivery completeness is performed by measuring the number of pancrelipase particles passing through the G-tube.
- enteric coating integrity is assessed on the recovered beads by visual inspection and by % of released lipase activity according to dissolution test (see above).

Instruments

G-tubes selected are tubes available on the market and are commonly used in clinical practice, and different types, stoma lengths and outer diameter are used. They are: Kimberly-Clark® MIC® Bolus with outer diameter: 16-18-20 Fr; Bard® Tri-Funnel outer diameter: 16-18-20 Fr Kimberly-Clark® MIC-KEY® with stoma length: 1.7-3.0-5.0 cm, outer diameter: 16, 18, 20 Fr (18 Fr=6 mm i.e. 1 French is exactly ⅓ millimeters. In SI units 1 French is $3.333 \; 10^{-4}$ meters; Bard® Tri-Funnel, outer diameter: 16, 18, 20 Fr); MiniONE® with stoma length: 1.7-3.0-4.4 (for 16 Fr) and 1.7-3.0-5.0 cm, (for 18 Fr), outer diameter: 16, 18 Fr; Bard® Button: 1.7-3.4-4.4 (for 18 and 24 Fr), 1.5-2.7-4.3 (for 28 Fr); outer diameter: 18 Fr.

Syringes used are: 35 mL catheter tip syringe Kimberly-Clark® in G-tube MIC-KEY® kit and 10 mL slip tip Terumo®.

EXAMPLES

Example 1. Stability of Pancrelipase Particles in Presence of Soft Foods

Stability of pancrelipase particles (Ultresa® 13,800 IU USP/cps) in presence of soft food is assessed to ensure that the contact with administrable nutritional medium is not detrimental to enteric coating (integrity). One Ultresa® capsule (13,800 IU USP/cps) is suspended for 60 minutes in 20 mL of soft food. Dissolution tests is performed on the samples and results (% of lipase released from Ultresa® minitablets/lipase activity) are reported here under.

TABLE 1

| Administrable nutritional medium | pH | Lipase relased from capsules (%) | | | | | | mean | SD | CV (%) |
|---|---|---|---|---|---|---|---|---|---|---|
| Applesauce $3^{rd}$ Food (Gerber ®) | 3.6 | 100 | 94 | 98 | 96 | 96 | 94 | 96 | 2.3 | 2 |
| Appleasauce (Beech-Nut) | 3.7 | 101 | 101 | 101 | 98 | 101 | 101 | 101 | 1.1 | 1 |
| Apple, Banana and Peach $3^{rd}$ Food (Gerber ®) | 3.9 | 103 | 105 | 103 | 103 | 90 | 101 | 101 | 5.5 | 5 |

Soft foods do not interact with the enteric coating (same has been verified for Zenpep® pancrelipase particles). In fact, dissolution data are in accordance with dissolution limits of USP chapter <711> Table 4 limits for delayed-release dosage form. Therefore, these soft foods can be safely used in combination with pancrelipase particles having an enteric coating.

Example 2. Preparation of Compositions Containing Pancrelipase Particles and G-Tube Administration Composition for G-tube administration of pancrelipase particles are prepared with amount corresponding to two capsules of dosage strength 5,000 IU USP (Zenpep® microtabs) (Samples C1-C5, C8-C9, A1-A3) and with Creon® in amount corresponding to 24,000 IU USP (sample C6-C7). They are prepared with the following method (method C): take the amount corresponding to the above dosage strengths of pancrelipase bead and pour the particles into a small cup remove the plunger from the selected syringe; cover the syringe tip with your finger, and pour an appropriate volume of administrable nutritional medium into the syringe barrel and then add the pancrelipase particles and the low viscosity oily ingredient if the test requires its presence; reattach the plunger and tilt the syringe tip upward; cover the tip with your finger, shake the syringe up and down vigorously for an appropriate time to disperse the particles; eliminate excess air from syringe, inject the mixture of pancrelipase/administrable nutritional medium into the feeding tube with a steady push until all of the mixture is delivered.

Samples A1-A3 are prepared in presence of the low viscosity oily ingredient. Sunflower seeds oil is added in amount of: 5%, 10% and 25% v/v of oil and volume of baby food (volume/volume) of Applesauce $3^{rd}$ Food (Gerber®). Samples C1-C5 are prepared for comparative purposes: sample C1-C4 do not have the low viscosity oily ingredient, whereas samples C8 and C9 contain a high viscous ingredient (mayonnaise, Hellmann®'s Light), in the same amount as the low viscosity oily ingredient (5, 10, 25%, volume of mayonnaise/volume of soft food); in C9 there is no baby food.

The tests are carried out on the final mixtures (pancrelipase particles and baby food and low viscosity oily ingredient) using Kimberly-Clark® MIC-KEY® combined with Secure Lok G-tube system (14, 16 and 20 Fr) or Kimberly-Clark® MIC® Bolus (16, 18 and 20 Fr).

TABLE 2

| Sample | Low viscosity oily ingredient | G-tube | G tube diameter | Secur-Lok® adapter | Clogging |
|---|---|---|---|---|---|
| C1 SF1 | No | MIC-KEY® | 16 | Yes | Clogging |
| C2 SF1 | No | MIC-KEY® | 20 | No | Clogging |
| C3 SF1 | No | MIC® Bolus | 16 | No | Clogging |
| C4 SF1 | No | MIC® Bolus | 18 | No | Clogging |
| C5 SF2 | No | MIC-KEY® | 14 | yes | Clogging |
| C6 SF2 | No | MIC-KEY® | 14 | yes | Clogging |
| C7 SF2 | No | MIC® Bolus | 16 | No | Clogging |

Stoma length = 1.7 cm; 35 mL syringe catheter tip; Soft food 1 (SF1): Applesauce 3rd Food (Gerber®); Soft food 2 (SF2): Applesauce 1st Food (Gerber®); Soft food 3 (SF3): Applesauce (Mott's®); * high pressure is perceived during the administration through the syringe; C1-C5 contain Zenpep® particles; C6-C7 contains Creon® granules.

TABLE 3

| Sample | Low viscosity oily ingredient | G-tube | G tube diam (Fr) | Applesauce | Banana |
|---|---|---|---|---|---|
| A1 SF2 2 cps | sunflower seeds oil: baby food (5, 10, 25%) | MIC® Bolus | 16 | Clogging | Clogging ⅔ |
| A2 SF2, 2 cps | sunflower seeds oil: baby food (5, 10, 25%) | MIC® Bolus | 18 | no clogging no sticking G-tube patency unaltered | no clogging no sticking G-tube patency unaltered |
| A3 SF2 2 cps | sunflower seeds oil: baby food (5, 10, 25%) | MIC® Bolus | 20 | no clogging no sticking G-tube patency unaltered | no clogging no sticking G-tube patency unaltered |
| C8 2 cps | Mayonaise: food (2.5:10) | MIC-KEY® + Secur-Lok® adapter | 14 | no clogging, sticking, G-tube patency altered | — |
| C9 2 cps | Mayonaise - no baby food | MIC-KEY® + Secur-Lok® adapter | 14 | clogging sticking, G-tube patency altered | — |

C8-C9: 2 cps Zenpep® 5,000 IU USP

Samples C1-C4 (no addition of low viscosity oily ingredient) form clogging in G-tubes having different diameters, probably due to aggregation phenomenon. Different from mayonnaise, sunflower seeds oil gives good results for G-tube patency and suitable medium viscosity. In presence of mayonnaise the formulation is very viscous and very difficult to be aspirated into the syringe. This occurs independently from type of baby food or mayonnaise ratio. Moreover, mayonnaise remains stick onto the tubes walls thus negatively affecting the patency; therefore, it is not suitable for use in administration through feeding tubes.

The delivery of the whole dose is achieved with the composition containing the low viscosity oily ingredient for all the tested ratio (v/v) using a 18 Fr G-tube (MIC® Bolus). Some administration system having peculiar shape (such as Secur-Lok® system) may not be always optimal to deliver microtablets using the oily additive because of potential swirling motion of the particles near the G-tube inlet that may produce a certain disordered arrangement of the particles and hence clogging in G-tube. The strong backpressure in the G-tubes may induce clogging also in the Secur-Lok® adapter.

Example 3. Preparation of Composition Containing Pancrelipase Particles and G-Tube Administration Different from the previous example, flushing G-tube with 1 mL of sunflower seeds oil is done before the administration of pancrelipase microtablets (Zenpep®) mixed with the soft food alone (10 mL). Results obtained are the same as for A2 and A3.

Example 4. Preparation of Compositions Containing Pancrelipase Particles and G-Tube Administration Composition samples according to the invention (A4-A6) and comparative samples (C10-C13) are prepared with method C as in Example 2. Pancrelipase particles are Ultresa® minitablets, dosage form with 13,800 IU USP lipase. Administration test is carried out using pancrelipase particles Ultresa® minitablets using the 35 mL syringe catheter tip combined with MIC® Bolus or Bard® Tri-Funnel G-tubes. Applesauce $3^{rd}$ Food (Gerber®) and Banana $3^{rd}$ Food (Gerber®) are used.

TABLE 4

| Sample | Low viscosity oily ingredient | G-tube | G tube diam (Fr) | Applesauce $3^{rd}$ Food | Banana $3^{rd}$ Food |
|---|---|---|---|---|---|
| A4 | sunflower seeds oil | MIC ® Bolus | 16 | Clogging | Clogging |
| A5 | sunflower seeds oil | MIC ® Bolus | 18 | no clogging no sticking G-tube patency unaltered | no clogging no sticking G-tube patency unaltered |
| A6 | sunflower seeds oil | MIC ® Bolus | 20 | no clogging no sticking G-tube patency unaltered | no clogging no sticking G-tube patency unaltered |
| C10 | No | MIC ® Bolus | 16 | Clogging | Clogging |
| C11 | No | MIC ® Bolus | 18 | Clogging | Clogging |
| C12 | No | MIC ® Bolus | 20 | no clogging no sticking G-tube patency unaltered | no clogging no sticking G-tube patency unaltered |
| C13 | No | Bard ® Tri-Funnel | 20 | no clogging no sticking G-tube patency unaltered | no clogging no sticking G-tube patency unaltered |

Ultresa® minitablets in amount of 13,800 IU USP alone (no low viscosity oily ingredient, samples C10-12) is deliverable by 20 Fr G-tube, whereas the minitablets in presence of 5% (volume/volume) of sunflower seeds oil (samples A4-A6) added to soft food are deliverable with 18 Fr G-tubes and above. By using a low viscosity oily ingredient, the delivery can be carried out with a reduced diameter, i.e., 18 Fr, than in the one which has to be used when no low viscosity oily ingredient is added to the soft food, i.e. 20 Fr.

Example 5. Preparation of Compositions Containing Pancrelipase Particles and G-Tube Administration Preparation of different compositions is carried out using method C as previously described. The samples are prepared by adding a given amount of pancreatin particles (minitabs, microtabs, granules; Zenpep®: 5000 IU USP/cps (microtabs) and 10,000 IU USP/cps (minitabs) Creon® 24,000 or Kreon® 40,000 IU USP/cps; Panzytrat®: 40,000 IU FIP/cps) into the syringe together with low viscosity oily ingredient and 5 mL of baby food (Applesauce $3^{rd}$ Food, Gerber®). Syringe is then shaken and its content injected into the G-tube (Kimberly-Clark® MIC® Bolus 16 and 18 Fr and Bard® Tri-Funnel with 18 Fr). After administration, 5 mL of baby food and 10 mL of distilled water are poured into syringe and G-tube to ensure complete dose administration and followed by flushing to collect any remaining material. Different low viscosity oily ingredients (sunflower oil, extra virgin olive oil, rapeseed oil) are added in different amounts (¼-½ e 1 teaspoon).

TABLE 5

| Low viscosity oily ingredient | Amount of low viscosity oily ingredient (teaspoon) | Number of capsules | Clogging |
|---|---|---|---|
| MIC ® Bolus 18 Fr Minitablet Zenpep ® 10,000 IU USP/cps (about 200 mg/cps) | | | |
| rapeseed oil | ¼ | 1 | No |
| | ½ | 1 | No |
| | 1 | 1 | No |
| sunflower oil | ¼ | 1 | No |
| | ½ | 1 | No |
| | 1 | 1 | No |
| extra virgin olive oil | ¼ | 1 | No |
| | ½ | 1 | No |
| | 1 | 1 | no |
| MIC ® Bolus 18 Fr Microtablet Zenpep ® 5,000 IU USP/cps (about 100 mg) | | | |
| rapeseed oil | ¼ | 2 | No |
| | ½ | 2 | No |
| | 1 | 2 | No |
| sunflower oil | ¼ | 2 | No |
| | ½ | 2 | No |
| | 1 | 2 | No |
| extra virgin olive oil | ¼ | 2 | No |
| | ½ | 2 | No |
| | 1 | 2 | No |
| Bard ® Tri-Funnel 18 Fr Microtablet Zenpep ® 5,000 IU USP/cps (about 100 mg) | | | |
| rapeseed oil | ¼ | 2 | No |
| | ½ | 2 | No |
| | 1 | 2 | No |
| sunflower oil | ¼ | 2 | No |
| | ½ | 2 | No |
| | 1 | 2 | No |
| extra virgin olive oil | ¼ | 2 | No |
| | ½ | 2 | No |
| | 1 | 2 | No |

TABLE 6

| Low viscosity oily ingredient | Amount of low viscosity oily ingredient (teaspoon) | Number of capsules | Clogging |
|---|---|---|---|
| MIC ® Bolus 16 Fr Minitablet Zenpep ® 10,000 IU USP/cps (about 200 mg) | | | |
| rapeseed oil | ¼ | 1 | Yes |
| | ½ | 1 | Yes |
| | 1 | 1 | Yes |
| sunflower oil | ¼ | 1 | Yes |
| | ½ | 1 | Yes |
| | 1 | 1 | Yes |
| extra virgin olive oil | ¼ | 1 | Yes |
| | ½ | 1 | Yes |
| | 1 | 1 | Yes |
| MIC ® Bolus 16 Fr Microtablet Zenpep ® 5,000 IU USP/cps (100 mg) | | | |
| rapeseed oil | ¼ | 2 | Yes |
| | ½ | 2 | Yes |
| | 1 | 2 | Yes |
| sunflower oil | ¼ | 2 | Yes |
| | ½ | 2 | Yes |
| | 1 | 2 | Yes |
| extra virgin olive oil | ¼ | 2 | Yes |
| | ½ | 2 | Yes |
| | 1 | 2 | yes |

TABLE 7

| Low viscosity oily ingredient | Amount of low viscosity oily ingredient (teaspoon) | Number of capsules | Clogging |
|---|---|---|---|
| MIC ® Bolus 16 Fr Kreon ® 40,000 IU FIP/cps (about 600 mg/cps) | | | |
| rapeseed oil | ¼ | 1 | Yes |
| | ½ | 1 | Yes |
| | 1 | 1 | Yes |
| sunflower oil | ¼ | 1 | yes |
| | ½ | 1 | Yes |
| | 1 | 1 | Yes |
| extra virgin olive oil | ¼ | 1 | Yes |
| | ½ | 1 | Yes |
| | 1 | 1 | Yes |
| MIC ® Bolus 16 Fr Kreon ® 40,000 IU FIP/cps (about 600 mg/cps) | | | |
| rapeseed oil | ¼ | ½ | No |
| | ½ | ½ | No |
| | 1 | ½ | No |
| sunflower oil | ¼ | ½ | No |
| | ½ | ½ | No |
| | 1 | ½ | No |
| extra virgin olive oil | ¼ | ½ | No |
| | ½ | ½ | No |
| | 1 | ½ | No |
| MIC ® Bolus 16 Fr Creon ® 24,000 IU USP/cps (about 450 mg/cps) | | | |
| rapeseed oil | ¼ | 1 | No |
| | ½ | 1 | No |
| | 1 | 1 | No |
| sunflower oil | ¼ | 1 | No |
| | ½ | 1 | No |
| | 1 | 1 | No |
| extra virgin olive oil | ¼ | 1 | No |
| MIC ® Bolus 16 Fr Creon ® 24,000 IU USP/cps (about 450 mg/cps) | | | |
| rapeseed oil | ¼ | ½ | No |
| | ½ | ½ | No |
| | 1 | ½ | No |
| sunflower oil | ¼ | ½ | No |
| | ½ | ½ | No |
| | 1 | ½ | No |
| extra virgin olive oil | ¼ | ½ | No |
| | ½ | ½ | No |
| | 1 | ½ | No |
| MIC ® Bolus 16 Fr Panzytrat ® 40,000 IU FIP/cps (about 240 mg/cps) | | | |
| rapeseed oil | ¼ | 1 | Yes |
| | ½ | 1 | Yes |
| | 1 | 1 | Yes |
| sunflower oil | ¼ | 1 | Yes |
| | ½ | 1 | Yes |
| | 1 | 1 | Yes |
| extra virgin olive oil | ¼ | 1 | Yes |
| | ½ | 1 | Yes |
| | 1 | 1 | Yes |
| MIC ® Bolus 16 Fr Panzytrat ® 40,000 IU FIP/cps (about 240 mg/cps) | | | |
| rapeseed oil | ¼ | ½ | Yes |
| | ½ | ½ | No |
| | 1 | ½ | No |
| sunflower oil | ¼ | ½ | No |
| | ½ | ½ | No |
| extra virgin olive oil | ¼ | ½ | No |
| | ½ | ½ | No |

For Zenpep® product, this low viscosity oily ingredient addition allows the complete administration of all different types of products (minitablets 10,000 U USP/cps, microtablets 5,000-10,000 U USP/cps) with G-tubes having 18 Fr diameter when administered together with baby food without any risk of having clogging.

Half dose strength of Kreon® (40,000 IU FIP/cps) (whose granules have smaller dimension than Zenpep® or Panzytrat®) can be transported through 16 Fr tubes (Kimberly-Clark® MIC® Bolus and Bard® Tri-Funnel) when oily vehicle is added to the composition before delivery into the G-tube. Clogging effect does not occur with Creon® 24,000

IU USP/cps (weight average content is 450 mg): no clogging or sticking is observed when 16 Fr tubes are used; all type of low viscosity oily ingredients works similarly well. For Kreon®/Creon® products, the use of low viscosity oily ingredient gives the advantage of administering a higher dose (double amount) with lower amount of baby food as compared to what reported by Shlieout 2011.

Panzytrat® 40,000 IU FIPP/cps has also a high content average weight (of about 400 mg) and, differently from Kreon®, particles have bigger dimension and irregular shape. Consequently mainly tubes obstruction is here observed rather than clogging (in absence of low viscosity oily ingredient). This is confirmed by visual inspection. Administration of amount corresponding to 20,000 IU FIP in presence of low viscosity oily ingredient (½ teaspoon) allows the release of the dosage and ensures that no clogging occurs.

For Ultresa® minitablets, the addition of low viscosity oily ingredient also allows to administer the composition with a G-tube having reduced smaller diameter (18 instead of 20 Fr).

From the above it is herein clearly shown the advantage of enteral administration of pancrelipase particles (from different marketed digestive enzyme products) in presence of administrable nutritional medium and low viscosity oily ingredient. Different products on the market have different weights and the particles/granules have various dimensions and shapes that render the enteral administration cumbersome in clinical practice. The composition of the invention allows to solve the problem of having this high variability in the marketed products and also to administer higher dosage strengths.

It is herein also shown that the enteral administration of the different marketed multiparticulated enteric coated pancrelipase products (independently from their particle dimension and shape) can always be safely performed with dosage strengths of about 10,000 IU USP lipase or higher strengths with G-tubes of at about 18 French in presence of an administrable nutritional medium and low viscosity oily ingredient.

What is claimed:

1. A digestive enzyme composition comprising an enterically coated pancrelipase product having a lipase activity at least about 5,000 IU;
   an administrable nutritional medium in amount of about 5 mL per each about 20,000 to about 40,000 lipase IU; and
   a pharmaceutically acceptable low viscosity oily ingredient selected from the group of vegetable oils, synthetic oils, fatty acids, and mixtures thereof, wherein the low viscosity oily ingredient is added in amount of about 5% to about 25% volume/volume of administrable nutritional medium.

2. The composition of claim 1, wherein the enterically coated pancrelipase product has an enteric polymer layer.

3. The composition of claim 1, wherein the enterically coated pancrelipase product is a multiparticulated product.

4. The composition of claim 3, wherein the multiparticulated product is in the form of beads, powder, granules, tablets, spheres, minitablets, microtablets, microparticles, microspheres, microcapsules or micropellets.

5. The composition of claim 2 wherein the enteric polymer is selected from the group consisting of cellulose acetate phthalate, hydroxypropyl-methylcellulose phthalate, hydroxypropyl-methylcellulose acetate succinate, shellac, methylmethacrylate copolymer, and methacrylic acid/methylmethacrylate copolymer, and methacrylic acid-ethyl acrylate copolymer (1:1).

6. The composition of claim 1, wherein the pancrelipase product is in therapeutically effective amount.

7. The composition of claim 1, wherein the administrable nutritional medium is an administrable nutritional medium, a nutritional formula, a soft food.

8. The composition of claim 7, wherein the administrable nutritional medium is a baby food.

9. The composition of claim 1, wherein the vegetable oil is selected from the group consisting of sunflower oil, olive oil, extra virgin olive oil, wheat germ oil, codliver oil, borage oil, sesame oil, soybean oil, arachis oil, corn oil, cottonseed oil, linseed oil, coconut oil, rapeseed oil, sesame oil, peanut oil, safflower oil, sweet almond oil, and apricot kernel oil, or mixture thereof.

10. The process for the preparation of the digestive enzyme composition of claim 1 comprising mixing the enterically coated pancrelipase product, administrable nutritional medium, pharmaceutically acceptable low viscosity oily ingredient.

11. The process of claim 10, wherein the enterically coated pancrelipase product, administrable nutritional medium, and low viscosity oily ingredient are either sequentially added and mixed in a container and then the composition is poured in a syringe, or they are partially added and mixed in a container, partially added in a syringe and then they admixed together in the syringe, or they are added directly in a syringe and mixed herein.

12. The process of claim 10, comprising the steps of: 1) adding enterically coated pancrelipase into a container; 2) placing an administrable nutritional medium in a syringe barrel followed by the pancrelipase particles and then a low viscosity oily ingredient; 3) shaking the syringe up and down vigorously to disperse the pancrelipase particles in the obtained composition; and 4) eliminating excess of air from syringe.

13. The process of claim 10, comprising the steps of: 1) placing an administrable nutritional medium in a syringe; 2) adding enterically coated pancrelipase particles thereto; 3) adding the low viscosity oily ingredient thereto; 4) shaking the syringe to disperse the pancrelipase particles in the obtained composition; and 5) eliminating excess of air from syringe.

14. A method of treating a pediatric or adult patient in need of the digestive enzyme composition of claim 1 comprising enterally administering to the patient the digestive enzyme composition.

15. The method of claim 14, wherein the enterically coated pancrelipase product is in a therapeutically effective amount of about 5,000 IU USP lipase or greater, administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube used for the enteral administration has internal diameter of at least about 18 Fr.

16. The method of claim 15, wherein the enterically coated pancrelipase product is in a therapeutically effective amount of about 10,000 IU USP lipase or greater, the administrable nutritional medium is present in amount of about 2 mL to about 15 mL per each about 5,000 to about 20,000 lipase IU USP of the pancrelipase product, the low viscosity oily ingredient is present in amount of about 5% to about 25% volume/volume of administrable nutritional medium, and the G-tube used for the enteral administration has internal diameter of at least about 18 Fr.

17. The method of claim 15, wherein the administrable nutritional medium is soft food and the low viscosity oily ingredient is vegetable oil.

18. The method of claim 17, wherein the administrable nutritional medium is baby food and the low viscosity oily ingredient is sunflower seed oil.

* * * * *